United States Patent [19]

Haefner et al.

[11] Patent Number: 5,662,688
[45] Date of Patent: Sep. 2, 1997

[54] SLOW GAIN CONTROL

[75] Inventors: Paul A. Haefner, Crystal; Mark A. Stockburger, Inver Grove Heights, both of Minn.

[73] Assignee: Cardiac Pacemakers, Inc., St. Paul, Minn.

[21] Appl. No.: 514,931

[22] Filed: Aug. 14, 1995

[51] Int. Cl.$^6$ ................................ A61N 1/39
[52] U.S. Cl. ................ 607/5; 128/708; 128/901
[58] Field of Search .................. 607/4, 5, 9; 128/696, 128/697, 704, 708, 901

[56] References Cited

U.S. PATENT DOCUMENTS

| | | |
|---|---|---|
| 3,590,811 | 7/1971 | Harris . |
| 3,878,833 | 4/1975 | Arneson et al. . |
| 3,927,677 | 12/1975 | Goebeli et al. . |
| 3,939,824 | 2/1976 | Arneson et al. . |
| 3,986,496 | 10/1976 | Brastad . |
| 3,999,556 | 12/1976 | Alferness . |
| 4,000,461 | 12/1976 | Barber et al. ............ 128/708 |
| 4,226,245 | 10/1980 | Bennett, Jr. . |
| 4,240,442 | 12/1980 | Andresen et al. . |
| 4,250,883 | 2/1981 | Thompson . |
| 4,325,384 | 4/1982 | Blaser et al. ............ 128/696 |
| 4,617,938 | 10/1986 | Shimoni et al. ............ 128/708 |
| 4,665,919 | 5/1987 | Mensink et al. . |
| 4,708,144 | 11/1987 | Hamilton et al. . |
| 4,722,351 | 2/1988 | Phillipps et al. ............ 128/696 |
| 4,766,902 | 8/1988 | Schroeppel . |
| 4,768,511 | 9/1988 | DeCote, Jr. . |
| 4,779,617 | 10/1988 | Whigham . |
| 4,819,643 | 4/1989 | Menken . |
| 4,827,934 | 5/1989 | Ekwall . |
| 4,880,004 | 11/1989 | Baker, Jr. et al. . |
| 4,903,699 | 2/1990 | Baker, Jr. et al. . |
| 4,934,376 | 6/1990 | Armington ............ 128/696 |
| 4,940,054 | 7/1990 | Grevis et al. . |
| 4,966,146 | 10/1990 | Webb et al. . |
| 4,967,747 | 11/1990 | Carroll et al. . |

(List continued on next page.)

FOREIGN PATENT DOCUMENTS

| | | |
|---|---|---|
| 0 321 764 | 12/1987 | European Pat. Off. . |
| 0340045 | 11/1989 | European Pat. Off. . |
| 0349130 | 1/1990 | European Pat. Off. . |
| 0350160 | 1/1990 | European Pat. Off. . |
| 0 451 498 | 10/1991 | European Pat. Off. . |
| 0580894 | 2/1994 | European Pat. Off. . |
| 0653225 | 5/1995 | European Pat. Off. . |
| 1466 707 | of 0000 | U.S.S.R. . |

OTHER PUBLICATIONS

P.I. Bennett, et al., "Portable Defibrillator–Monitor for Cardiac Resuscitation," *Hewlett–Packard Journal*, vol. 3, pp. 22–28 (Feb. 1982).

A.F. Rickards, et al., "The Use of QT Interval to Determine Pacing Rate: Early Clinical Experience," *PACE*, 6, pp. 346–354 (Mar.–Apr. 1983).

N.V. Thakor, et al., "Design and Evaluation of QRS and Noise Detectors for Ambulatory E.C.G. Monitors," *Med. & Biol. Eng. & Comput.*, 20, pp. 709–714 (1982).

N.V. Thakor, et al., "A Circuit for Minimizing False Alarms in Computerized ECG Monitoring," *IEEE 1979 Frontiers of Engineering in Health Care*, IEEE/Engineering in Medicine & Biology Society Conference, pp. 16–19 (Oct. 6–7, 1979).

(List continued on next page.)

Primary Examiner—Jeffrey R. Jastrzab
Attorney, Agent, or Firm—Schwegman, Lundberg, Woessner & Kluth, P.A.

[57] ABSTRACT

A system and method automatically controls a gain of a cardioverter/defibrillator which receives electrical activity of the heart and delivers shock pulses in response thereto. An amplifier amplifies the electrical activity according to a variable gain. A detection circuit detects depolarizations in the amplified electrical activity and provides a detect signal representing a cardiac event indicative of a depolarization when the amplified electrical activity exceeds a sensitivity threshold. A storage device stores peak history information representative of peak values of the amplified electrical activity of a first selected number (N) of cardiac events. Slow gain control circuitry adjusts the variable gain in discrete steps based on the stored peak history information.

60 Claims, 7 Drawing Sheets

U.S. PATENT DOCUMENTS

| | | | |
|---|---|---|---|
| 4,972,835 | 11/1990 | Carroll et al. | |
| 5,010,887 | 4/1991 | Thornander | 128/696 |
| 5,014,704 | 5/1991 | Alt | |
| 5,050,599 | 9/1991 | Hoegnelid | 128/419 |
| 5,065,766 | 11/1991 | Sasaki | 128/708 |
| 5,103,819 | 4/1992 | Baker et al | |
| 5,117,824 | 6/1992 | Keimel et al. | |
| 5,269,300 | 12/1993 | Kelly et al. | 607/4 |
| 5,330,508 | 7/1994 | Gunderson | 607/14 |
| 5,339,820 | 8/1994 | Henry et al. | 128/696 |
| 5,354,316 | 10/1994 | Keimel | 607/15 |
| 5,370,124 | 12/1994 | Dissing et al. | 128/696 |
| 5,374,282 | 12/1994 | Nichols et al. | 607/18 |
| 5,417,221 | 5/1995 | Sickler | 128/696 |
| 5,458,621 | 10/1995 | White et al. | 607/5 |
| 5,470,342 | 11/1995 | Mann et al. | 607/5 |
| 5,513,644 | 5/1996 | McClure et al. | 128/708 |

OTHER PUBLICATIONS

N.V. Thakor, et al., "Optimal QRS Filter," *IEEE 1980 Frontiers of Engineering in Health Care*, IEEE/Engineering in Medicine & Biology Society Conference, pp. 190–195 (Sep. 28–30, 1980).

N.V. Thakor, "Design, Implementation, and Evaluation of a Microcomputer–Based Portable Arrhythmia Monitor," Thesis paper submitted at the University of Wisconsin–Madison (1981).

N.V. Thakor, "Reliable R–Wave Detection From Ambulatory Subjects," *Biomedical Sciences Instrumentation*, 14, Proceedings of the 15th Annual Rocky Mountain Engineering Symposium, pp. 67–72 (Apr. 17–18, 1978).

"R–Wave Detector," *Design of Microcomputer–Based Medical Instrumentation*, book edited by W.J. Tompkins and J.G. Webster, pp. 413–415 (1981).

R.A. Winkle, et al., "The Automatic Implantable Defibrillator: Local Ventricular Bipolar Sensing to Detect Ventricular Tachycardia and Fibrillation," *Am. Journ. of Cardiology*, 52, pp. 265–270 (Aug. 1983).

J.G. Webster, et al., "A Portable, Microcomputer–Based ECG Arrhythmia Monitor," *Proceedings of the 31st Annual Conference on Engineering in Medicine & Biology*, vol. 20, p. 60 (Oct. 21–25, 1980).

Igor Singer et al., "The Automatic Implantable Cardioverter Defibrillator: T Wave Sensing in the Newest Generation," *PACE*, 11, 1584–1591 (Nov. 1988).

N.V. Thakor et al., "Optimal QRS Detector," *Med. & Biol. Eng. & Comput.*, 21, 343–350 (May 1983).

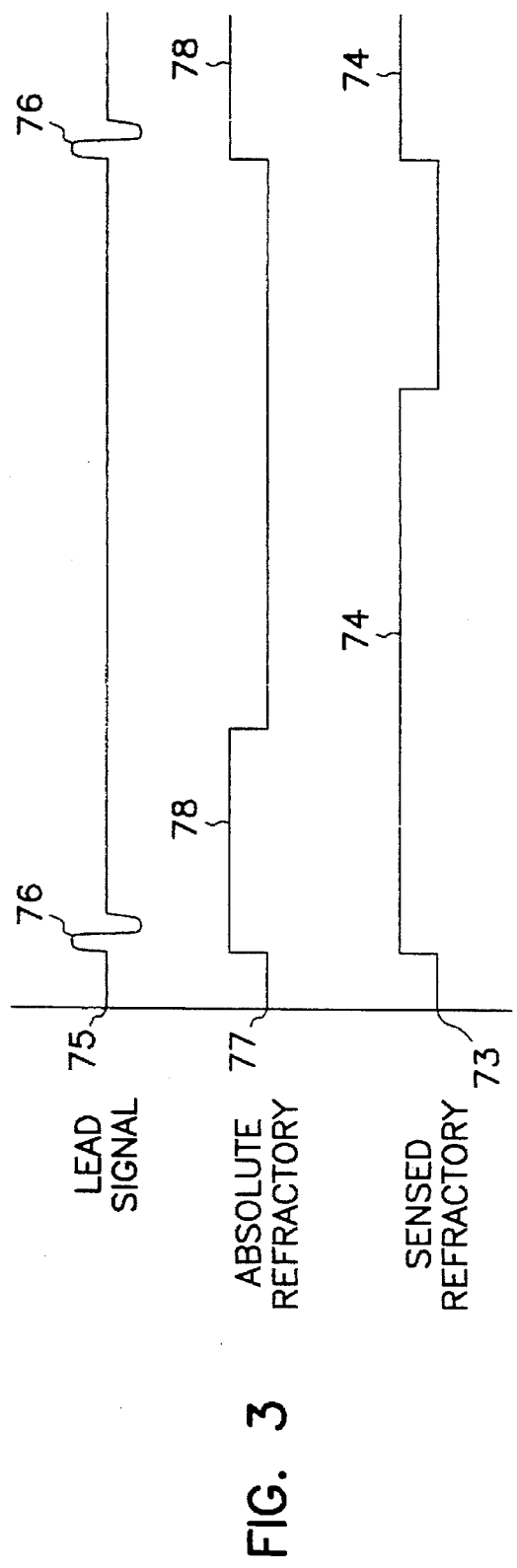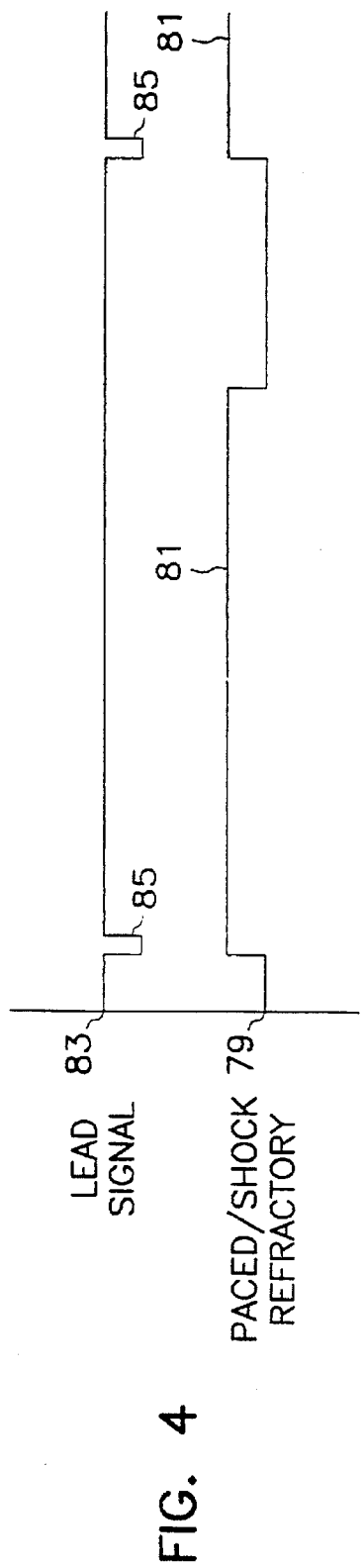

SLOW GAIN CONTROL

FIELD OF THE INVENTION

The present invention relates generally to implantable medical devices, and more particularly, to systems such as automatic gain control systems for automatically adjusting the sensing threshold in cardiac rhythm management devices, such as pacemakers, cardioverter/defibrillators, and cardioverter/defibrillators with pacing capability.

BACKGROUND OF THE INVENTION

Cardiac rhythm management devices such as pacemakers, cardioverter/defibrillators, and cardioverter/defibrillators with pacing capability typically include a system for detecting dangerous cardiac arrhythmia conditions in the heart, such as bradycardia, tachycardia, and fibrillation by measuring the time interval between consecutive cardiac depolarizations. Cardiac rhythm management devices receive a sensed cardiac signal comprising electrical activity of the heart and detect cardiac depolarizations in the electrical activity when an amplitude of the electrical activity exceeds a predetermined amplitude level or "sensing threshold." The sensing threshold may be fixed, or may vary over time.

A fixed sensing threshold is not appropriate for detecting certain arrhythmias, such as polymorphic tachycardia and fibrillation, wherein extreme variations occur in the amplitude of the electrical activity during the arrhythmia. The problem of tracking variations in the amplitude of the electrical activity is further complicated when the cardiac rhythm management device delivers pace pulses to the heart, which cause invoked responses which are quite high in amplitude as compared to normal cardiac depolarizations.

One approach to compensate for problems associated with a fixed sensing threshold is to program the sensing threshold at a value determined by the attending physician after careful study of the variety of amplitudes in cardiac signal activity experienced by a patient. In other words, a sensing threshold is programmed into the cardiac rhythm management device, and any cardiac signal amplitude larger than the programmed sensing threshold is considered a cardiac depolarization. If, however, the programmed sensing threshold is set too high and the cardiac signal amplitude decreases significantly, as is often the case in fibrillation, the cardiac rhythm management device may not sense the arrhythmia. If the programmed sensing threshold is set too low, the device may over-sense. For example, a system designed to detect ventricular depolarizations (R-waves) may erroneously detect atrial depolarizations (P-waves) or ventricular recovery (T-waves). Bandpass filtering can be used to partially eliminate erroneous detection of the P-waves and T-waves in a R-wave detection system. If, however, the band of frequencies passed by the bandpass filtering is too narrow, certain fibrillation signals may not be detected.

Another approach to compensate for the above problems is to set the sensing threshold proportional to the amplitude of the sensed cardiac signal each time a cardiac depolarization is sensed. The sensing threshold is then allowed to decrease over time between consecutively sensed cardiac depolarizations so that if the sensed cardiac signal amplitude decreases significantly, the cardiac rhythm management device is still able to detect the lower level amplitude of the cardiac signal. Adjusting the sensing threshold to an appropriate level with this approach becomes difficult if the patient requires pacing due to a bradycardia condition. For example, in a system that senses R-waves according to this approach, the sensing threshold may be adjusted to one-half of the R-wave amplitude when an R-wave is sensed. However, the invoked response due to a first pacing pulse can cause the sensing threshold to be set so high that a second spontaneous R-wave is not sensed. Because the system does not sense the second spontaneous R-wave, a second pacing pulse is delivered to the patient inappropriately.

One solution to the above problem is found in the Kelly et al. U.S. Pat. No. 5,269,300 assigned to Cardiac Pacemakers, Inc., the assignee of the present application. The Kelly et al. patent discloses an implantable cardioverter/defibrillator with pacing capability wherein the sensing threshold is automatically adjusted to a value proportional to the amplitude of the sensed cardiac signal. The sensing threshold continuously decreases between sensed cardiac depolarizations to ensure that a lower level cardiac signal will be detected. However, after a pacing pulse is delivered by the Kelly et al. device, the sensing threshold is set to a fixed value, and held at the fixed value for a predetermined period of time, so that the sensing threshold is not affected by the cardiac response invoked by the pacing pulse. After a predetermined period of time, the sensing threshold is decreased, just as after a spontaneous cardiac depolarization.

In the Keimel et al. U.S. Pat. No. 5,117,824, an R-wave detector automatically adjusts the detecting threshold in response to the R-wave amplitude. The adjustment of the threshold is disabled for a predetermined period following the delivery of each pacing pulse. Thereafter, the sensing threshold is returned to a lower threshold level to allow detection of lower level R, waves indicative of tachyrhythmia conditions.

In the Henry et al. U.S. Pat. No. 5,339,820, a sensitivity control is used for controlling a sensing threshold in a cardiac control device such as a pacemaker, cardioversion and/or cardiac defibrillation device. Initially, a sensing threshold is set to a low value. When the cardiac signal is detected, the amplitude of the R-wave is measured and the sensing threshold is computed as a function of the amplitude of the R-wave. After a refractory period, the sensing threshold is preferably set to 75% of the amplitude of the R-wave. The sensing threshold is then decreased in uniform steps. The uniform steps may be fixed decrements or percentage reductions.

The Grevis et al. U.S. Pat. No. 4,940,054 discloses a cardioversion device having three sensitivities. A first, medium sensitivity is used for the detection of sinus rhythm and ventricular tachycardia. A second, higher sensitivity is designed for differentiating ventricular fibrillation from asystole. A third, lower sensitivity is used to differentiate between R-waves and high amplitude current of injury T-waves which occur after shocking. One of these three sensitivities is selected as a function of the status of the device, such as during a period of suspected tachycardia or a post shock period, and the selected sensitivity must be maintained at least until the next cycle.

The Dissing et al. U.S. Pat. No. 5,370,124 discloses a cardiac rhythm management device having circuitry for automatically adapting the detection sensitivity to the cardiac signal. The detection sensitivity is adjusted by either amplifying the electrical signal supplied to the threshold detector with a variable gain given a permanently prescribed threshold or by varying the threshold itself. In either case, the effective threshold is based on an average value formed over a time interval corresponding to the duration of a few breaths. A switching hysteresis is generated having a lower limit value and an upper limit value, where the threshold is reset only when the average value falls below the lower limit value or exceeds the upper limit value. The limit values of the switching hysteresis are varied with the variation of the threshold, but the relationship of the limit values to the threshold remain unvaried. In one embodiment of the Dissing device, when the threshold is set below a minimum value, a beat-to-beat variance of signal heights of successive input electrical signals are used for forming an average value. The sensing threshold is raised by a predetermined amount if the variance exceeds the predetermined variance value.

The Carroll et al. U.S. Pat. No. 4,972,835 discloses an implantable cardiac defibrillator which includes switched capacitor circuitry for amplifying the cardiac electrical signal with non-binary gain changing steps. Three stages of gain are used to increase the gain approximately 1.5 each increment.

The Baker et al. U.S. Pat. No. 5,103,819 discloses a state machine for automatically controlling gain of the sensing function in an implantable cardiac stimulator. The rate of gain adjustment is dependent on the present sensed conditions and on the prior state of the heart. Different rates of adjustment are selected under varying conditions so that the gain of the sense amplifier is adjusted without significant overshoot. Multiple effective time constants are used for different conditions by basing the rate of adjustment of the sense amplifier gain on the path traversed in the state machine.

Therefore, considerable effort has been expended in providing for automatically adjustable sensing thresholds through adjusting the threshold level itself or with automatic gain circuitry in implantable cardiac rhythm management devices for the purpose of enhancing the capability of the device to sense arrhythmia conditions for which therapy is to be applied.

SUMMARY OF THE INVENTION

The present invention provides a method and system for automatically controlling a gain of a cardioverter/defibrillator which receives electrical activity of the heart and provides shock pulses in response to the received electrical activity. An amplifier amplifies the electrical activity of the heart according to a variable gain. A cardiac depolarization detector detects depolarizations in the amplified electrical activity of the heart and provides a detect signal representing a cardiac event indicative of a depolarization when the amplified electrical activity exceeds a sensitivity threshold. A storage device stores peak history information representative of peak values of the amplified electrical activity of a first selected number (N) of cardiac events. A gain controller adjusts the variable gain in discrete steps based on the stored peak history information.

The gain controller preferably increases the variable gain by at least one discrete step if a second selected number (M) of peak values of the N cardiac events are below a selected low threshold and decreases the variable gain by at least one discrete step if M peak values of the N cardiac events are above a selected high threshold. The value of M is preferably at least 3 and the value of N is preferably at least 4. The peak history information from the previous cardiac event is updated in the storage device preferably at the beginning of a new refractory period caused by a cardiac event. The storage device preferably includes a first group of storage locations which store peak information indicating if the peak values are below the selected low threshold and a second group of storage locations which store peak information indicating if the peak values are above the selected high threshold.

In a preferred embodiment of the present invention, the gain controller increases the variable gain if a stored peak value of a last cardiac event and M-1 peak values of the last N-1 cardiac events previous to the last cardiac event are below the selected low threshold and decreases the variable gain if the stored peak value of the last cardiac event and the M-1 peak values of the last N-1 cardiac events previous to the last cardiac event are above the selected high threshold.

In a preferred embodiment of the present invention, the gain controller includes a storage device capable of storing peak history information representative of peak values of amplified electrical activity of a third selected number of cardiac events. In this embodiment, far field sense circuitry responds to the stored peak history information to indicate a decrease in the variable gain if the peak values of the amplified electrical activity of the third selected number of cardiac events alternate between clipped peak values and non-clipped peak values. The peak value is determined to be clipped if the peak value is at a maximum peak value. In the preferred embodiment of the present invention, the gain controller is implemented in digital circuitry, which permits a simple comparison to a maximum digital value to determine whether or not a peak value has been clipped. The third selected number can be equal to the first selected number. In the embodiment of the present invention where M is equal to 3 and N is equal to 4, the third selected number is preferably set to a value of 6 which requires two extra storage locations in the storage device.

In a preferred embodiment of the present invention, the gain controller includes circuitry responsive to the detect signal to set the gain to a selected relatively high sensitivity if a cardiac event is not detected for a selected time period. For example, a suitable selected time period is approximately 1.5 seconds which is equivalent to approximately 40 heart beats per minute. The selected relatively high sensitivity is preferably at least one discrete gain step from a maximum sensitivity. The gain controller also preferably includes circuitry to set the gain to the selected relatively high sensitivity when the cardioverter/defibrillator delivers a shock pulse to the heart. In the cardioverter/defibrillator with pacing capability embodiment of the present invention, the gain controller also preferably includes circuitry to set the gain to the selected relatively high sensitivity when the cardioverter/defibrillator delivers a pacing pulse to the heart.

The gain controller preferably includes circuitry to decrement the gain from the selected relatively high sensitivity by a selected number of discrete gain steps if the setting of the gain to the selected relatively high sensitivity creates a clipped peak value of the amplified electrical activity on the following detected cardiac event. The circuitry preferably further decrements the gain by at least one discrete gain step if the peak value of the amplified electrical activity is still clipped on the second detected cardiac event following the setting of the gain to the selected relatively high sensitivity. In addition, the circuitry preferably decrements the gain from the selected relatively high sensitivity by a selected number of discrete gain steps if the setting of the gain to the selected relatively high sensitivity does not create a clipped peak value of the amplified electrical activity on the following detected cardiac event and does create a clipped peak value of the amplified electrical activity on the second detected cardiac event following the setting of the gain to the selected relatively high sensitivity.

BRIEF DESCRIPTION OF THE DRAWINGS

FIG. 3 is a timing diagram illustrating the sensed refractory used in the cardioverter/defibrillator of FIG. 1.

FIG. 4 is a timing diagram illustrating the paced/shock refractory used in the cardioverter/defibrillator of FIG. 1.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Dual Chamber Cardioverter/Defibrillator with Pacing Capability

Figure 1:
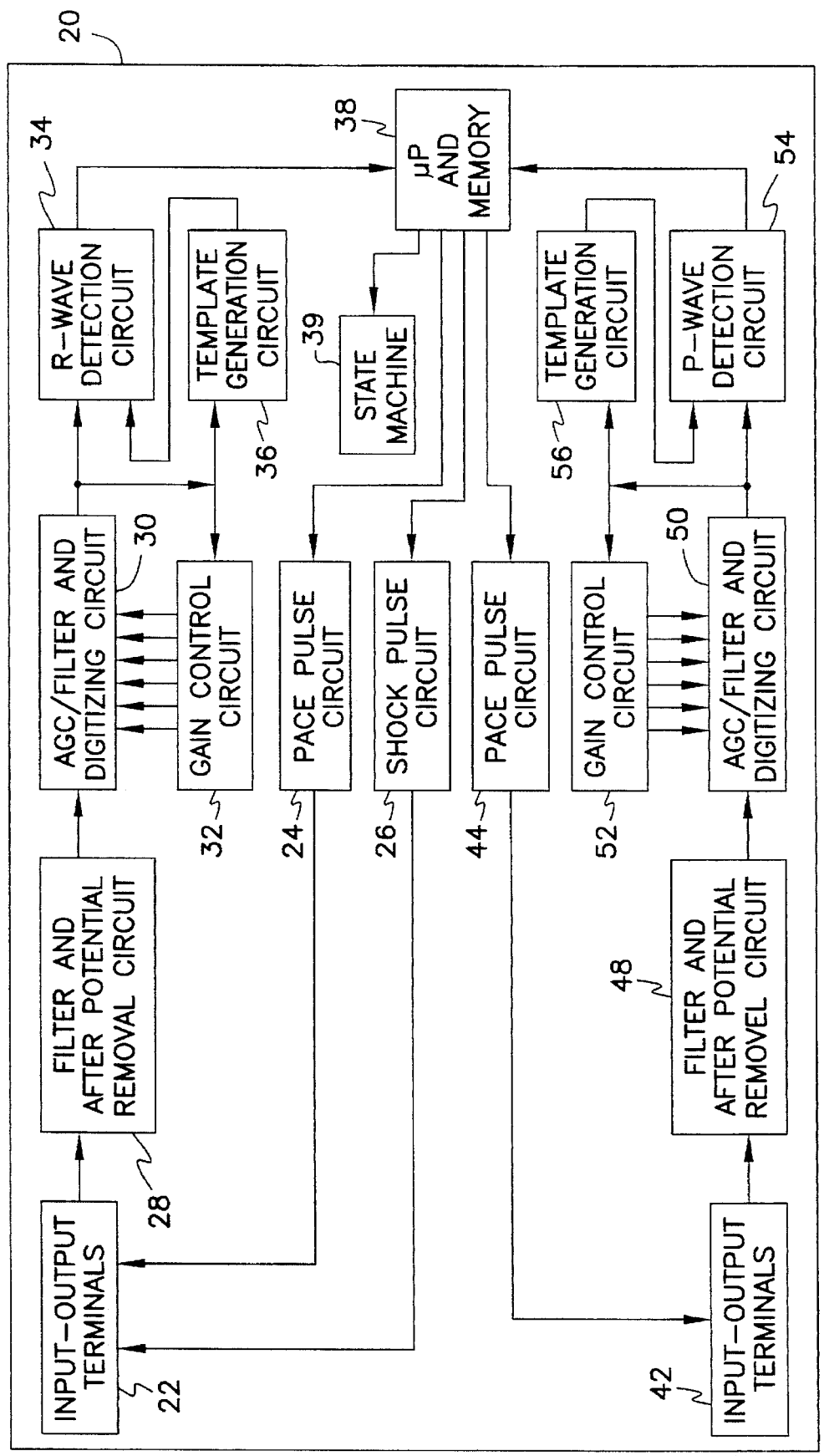
FIG. 1 is a block diagram of a dual chamber cardioverter/defibrillator according to the present invention.

A dual chamber cardioverter/defibrillator 20 with pacing capability is illustrated in block diagram form in FIG. 1. Cardioverter/defibrillator 20 operates as a pulse generator device portion of a cardiac rhythm management system which also includes leads or electrodes (not shown) disposed in the ventricular chamber of the heart to sense electrical activity representative of a R-wave portion of the PQRST complex of a surface EGM indicating depolarizations in the ventricle. Cardioverter/defibrillator 20 includes input/output terminals 22 which are connectable to the ventricular leads to receive the ventricular electrical activity of the heart sensed by the ventricular leads. A pace pulse circuit 24 provides pacing pulses such as bradycardia and antitachycardia pacing pulses to input/output terminals 22 to be provided to the ventricular chamber of the heart via the ventricular leads to stimulate excitable myocardial tissue to treat arrhythmia conditions such as bradycardia and some tachycardia. A shock pulse circuit 26 provides shock pulses to input/output terminals 22 to be provided to the ventricular chamber of the heart via the ventricular leads to shock excitable myocardial tissue to treat tachyrhythmia conditions. The tachyrhythmia conditions may include either ventricle fibrillation or ventricle tachycardia.

A filter and after potential removal circuit 28 filters the ventricular electrical activity received by input/output terminals 22 and the pacing pulses provided from pacing pulse circuit 24. In addition, filter and after potential removal circuit 28 removes after potential created by a pacing pulse from pacing pulse circuit 24 or a shock pulse delivered by shock pulse circuit 26. A preferred after potential removal circuit is described in detail in the co-pending and commonly assigned U.S. patent application Ser. No. 08/492,199 entitled "AFTER POTENTIAL REMOVAL IN CARDIAC RHYTHM MANAGEMENT DEVICE" filed on Jun. 19, 1995, and which is incorporated herein by reference.

An automatic gain control (AGC)/filter and digitizing circuit 30 according to the present invention amplifies the filtered ventricular electrical activity provided from the filter and after potential removal circuit 28. AGC/filter and digitizing circuit 30 includes circuitry for digitizing the filtered ventricular electrical activity. A gain control circuit 32 automatically adjusts the gain of AGC/filter and digitizing circuit 30. An R-wave detection circuit 34 is coupled to AGC/filter and digitizing circuit 30 to detect depolarizations in the amplified ventricular electrical activity representative of R-wave depolarizations when the amplified ventricular electrical activity exceeds a selected amplified level known as the "sensitivity threshold" or the "sensing threshold" and refractory is inactive. A template generation circuit 36 automatically selects and adjusts the sensing threshold. R-wave detection circuit 34 provides a R-wave depolarization signal, indicative of the R-wave depolarizations, to a microprocessor and memory 38.

The cardiac rhythm management system also includes leads or electrodes (not shown) disposed in the atrial chamber of the heart to sense electrical activity representative of a P-wave portion of the PQRST complex of a surface EGM indicating depolarizations in the atrium. Cardioverter/defibrillator 20 correspondingly also includes input/output terminals 42 which are connectable to the atrial leads to receive the atrial electrical activity of the heart sensed by the atrial leads. A pace pulse circuit 44 provides pacing pulses such as bradycardia pacing pulses to input/output terminals 42 to be provided to the atrial chamber of the heart via the atrial leads to stimulate excitable myocardial tissue to treat arrhythmia conditions such as bradycardia or atrial tachycardia. A filter and after potential removal circuit 48 operates similar to filter and after potential removal circuit 28 to filter the atrial electrical activity received by input/output terminals 42 and the pacing pulses provided from pacing pulse circuit 44. In addition, filter and after potential removal circuit 48 removes after potential created by a pacing pulse from pacing pulse circuit 44.

An automatic gain control (AGC)/filter and digitizing circuit 50 according to the present invention amplifies the filtered atrial electrical activity provided from the filter and after potential removal circuit 48. AGC/filter and digitizing circuit 50 includes circuitry for digitizing the filtered atrial electrical activity. A gain control circuit 52 automatically adjusts the gain of AGC/filter and digitizing circuit 50. An P-wave detection circuit 54 is coupled to AGC/filter and digitizing circuit 50 to detect depolarizations in the amplified atrial electrical activity representative of P-wave depolarizations when the amplified atrial electrical activity exceeds a selected amplified level known as the "sensitivity threshold" or the "sensing threshold" and the refractory is inactive. A template generation circuit 56 automatically selects and adjusts the sensing threshold. P-wave detection circuit 54 provides a P-wave depolarization signal, indicative of the P-wave depolarizations, to microprocessor and memory 38.

Microprocessor and memory 38 analyzes the detected P-waves indicated in the P-wave depolarization signal from P-wave detection circuit 54 along with the R-wave depolarization signal provided from R-wave detection circuit 34 for the detection of arrhythmia conditions based on known algorithms. For example, microprocessor and memory 38 can be used to analyze the rate, regularity, and onset of variations in the rate of the reoccurrence of the detected P-wave and/or R-wave, the morphology of the detected P-wave and/or R-wave, or the direction of propagation of the depolarization represented by the detected P-wave and/or R-wave in the heart. In addition, microprocessor and memory 38 stores depolarization data and uses known techniques for analysis of the detected R-waves to control pace pulse circuit 24 and shock pulse circuit 26 for delivery of pace pulses and shock pulses to the ventricle and for analysis of detected P-waves to control pace pulse circuit 44 for proper delivery of pace pulses to the atrium. In addition, microprocessor and memory 38 controls a state machine 39 which places various circuits of cardioverter/defibrillator 20 in desired logical states based on various conditions such as when a pace pulse or shock pulse occurs or on operating conditions of the cardioverter/defibrillator such as bradycardia pacing, tachyrhythmia sensing, and normal sinus sensing.

The dual chamber cardioverter/defibrillator 20 with pacing capability illustrated in FIG. 1 includes pacing and shocking capabilities for the ventricle and pacing capability for the atrium. Nevertheless, the present invention can be embodied in a single chamber cardiac rhythm management device having a single one of these capabilities. For example, the present invention can be embodied in a ventricle defibrillator device for providing shock pulses to the ventricle only.

In some embodiments of cardioverter/defibrillator 20, input/output terminals 22 and 42 are each implemented to be connectable to a corresponding single set of electrodes (not shown) used for pacing, shock delivery, and sensing. In other embodiments of cardioverter/defibrillator 20, the input/output terminals are implemented to be connectable to separate sets of electrodes for pulse delivery and sensing. In some embodiments, the input/output terminals are implemented to be connectable to separate electrodes for pacing and shock delivery. In all of to these embodiments, the electrodes of a cardiac rhythm management system are typically implemented as unipolar or bipolar electrodes.

A unipolar electrode configuration has one pole or electrode. (i.e., negative pole or cathode electrode) located on or within the heart, and the other pole or electrode (i.e., positive pole or anode electrode) remotely located from the heart. With endocardial leads, for example, the cathode is located at the distal end of a lead and typically in direct contact with the endocardial tissue to be stimulated, thus forming a "tip" electrode. Conversely, the anode is remotely located from the heart, such as comprising a portion of the metallic enclosure which surrounds the implanted device, thus forming a "can" electrode and is often referred to as the "indifferent" electrode.

A bipolar electrode configuration has both poles or electrodes typically located within the atrial or ventricular chamber of the heart. With endocardial leads, for example, the cathode is located at the distal end of the lead, referred to as the "tip" electrode. In the bipolar configuration, the anode is usually located approximate to the "tip" electrode spaced apart by 0.5 to 2.5 cm., and typically forming a ring-like structure, referred to as the "ring" electrode.

With respect to sensing, it is well known that bipolar and unipolar electrode configurations do not yield equivalent cardiac EGMs. Each configuration has advantages and disadvantages, for example, with a unipolar-sensing configuration, only the electrical events adjacent to the "tip" electrode control the unipolar EGM, while the remote "indifferent" electrode contributes negligible voltage due to its location being extracardiac.

With a bipolar-sensing configuration, the magnitude of the cardiac signal is similar for both the "ring" and the "tip" electrodes, but the resulting EGM is highly dependent upon the orientation of the electrodes within the heart. Optimal sensing will occur, for example, when the sensing vector defined by the sensing electrodes is parallel with the dipole defined by the depolarization signal. Since bipolar electrodes are more closely spaced than their unipolar counterparts, the depolarization signal will be shorter in duration than that produced from a unipolar configuration. Due to a more restrictive lead field or antenna, bipolar sensing offers improved rejection of electromagnetic and skeletal muscle artifacts, and thus provides a better signal-to-noise ratio than unipolar sensing.

AGC/Filter and Digitizing Circuit

Figure 2:
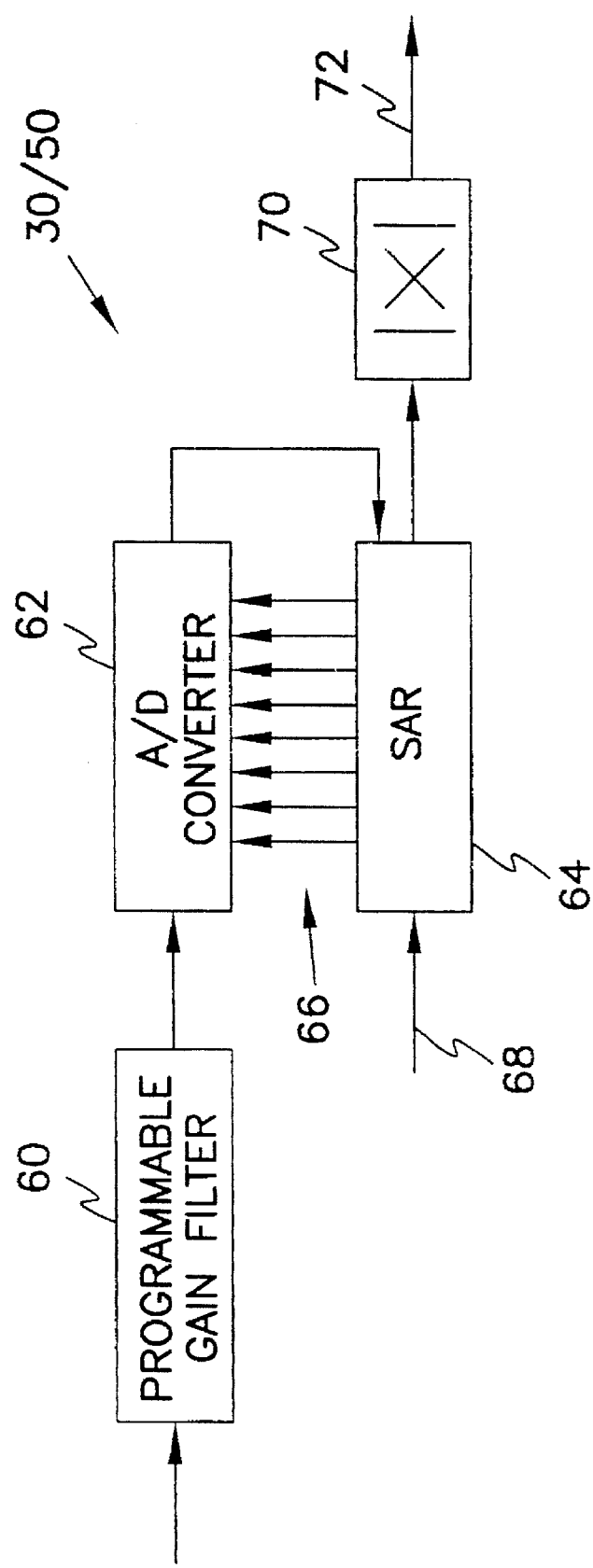
FIG. 2 is a logical block diagram of an AGC filter and digitizing circuit according to the present invention.

A logical block diagram representative of AGC/filter and digitizing circuit 30 or 50 is illustrated in FIG. 2. A programmable gain filter 60 filters the electrical activity provided from the filter and after potential removal circuit 28 or 48 of FIG. 1. When cardioverter/defibrillator 20 of FIG. 1 is implemented to be connectable to bipolar electrodes, programmable gain filter 60 comprises an analog differential sense amplifier to sense and amplify the difference between first and second bipolar electrodes. Programmable gain filter 60 has a programmable gain to initially amplify the incoming electrical activity.

An analog to digital (A/D) converter 62 receives the filtered and amplified electrical activity from programmable gain filter 60 and converts the analog electrical activity to digitized cardiac data, which is stored in a successive approximation register (SAR) 64. A/D converter 62 operates by comparing a sample of "unknown" analog electrical activity from programmable gain filter 60 against a group of weighted values provided from SAR 64 on lines 66. A/D converter 62 compares the weighted values on lines 66 in descending order, starting with the largest weighted value. A weighted value is not added to the summed digital data stored in SAR 64 if the weighted value, when added to the previous summed weighted values, produces a sum larger than the sampled "unknown" analog electrical activity. The summed digital data is updated in SAR 64 and a new weighted value is compared on each active edge of a SAR clock on a line 68.

At the end of the successive approximation when balance is achieved, the sum of the weighted values stored as the summed digital data in SAR 64 represents the approximated value of the sampled "unknown" analog electrical activity. SAR 64 provides the stored digital cardiac data to an absolute value circuit 70. Absolute value circuit 70 provides the absolute value of the amplitude of the digital cardiac data on a line 72 to be provided to gain control circuit 32/52 and template generation circuit 36/56. Successive approximation A/D conversion as performed by A/D converter 62 and SAR 64 is very fast to permit adequate tracking of the incoming analog cardiac signal. The gain of programmable gain filter 60 is raised or lowered in discrete gain steps based on outputs from gain control circuit 32/52.

Separate Gain Control and Threshold Templating

Gain control circuit 32/52 and template generation circuit 36/56 operate with the AGC/filter and digitizing circuit 30/50 to implement two independent AGC digital loops according to the present invention. Gain control circuit 32/52 provides slow gain control to AGC/filter and digitizing circuit 30/50 to keep sensed depolarizations representative of cardiac events in approximately the upper one third of the dynamic range of A/D converter 62. Template generation circuit 36/56 provides a fast responding variable sensing threshold to the detection circuit 34/54 for actual sensing of R-wave or P-wave depolarizations representative of cardiac events.

Gain control circuit 32/52, as described in more detail below with reference to FIG. 5, stores peak history information representative of peak values of the amplified electrical activity of a selected number (N) of cardiac events. Gain control circuit 32/52 adjusts the variable gain of AGC/filter and digitizing circuit 30/50 in discrete steps based on the stored peak history information. The stored peak history information is compared against predefined levels and appropriate gain changes are initiated based on a second selected number (M) of peak values of the N cardiac events being outside of a selected range.

Figure 7:
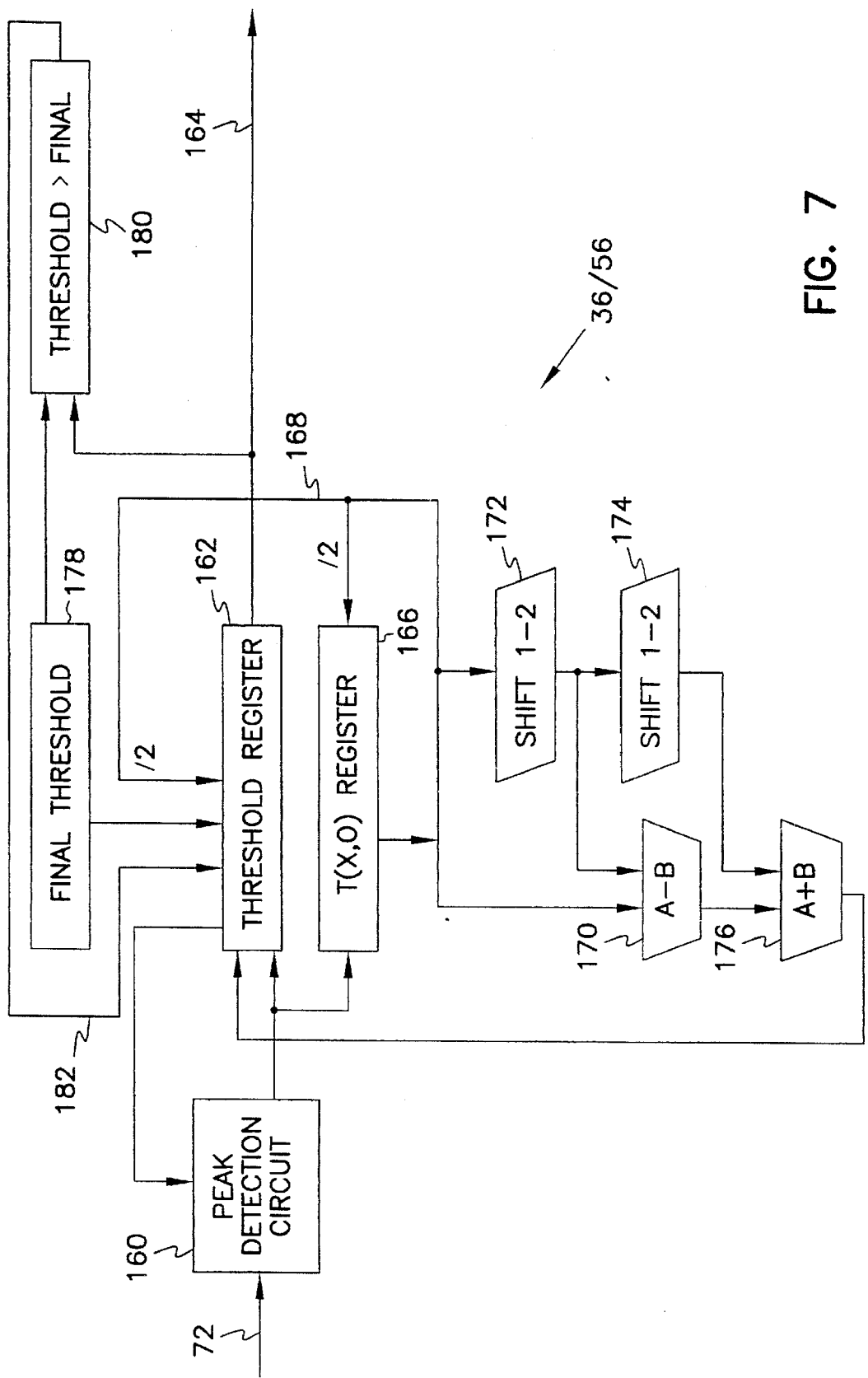
FIG. 7 is a template generation circuit according to the present invention, which achieves the piecewise linear approximation of an exponential decay illustrated in FIG. 6.

Template generation circuit 36/56, as described in more detail below with reference to FIG. 7, provides a time varying sensing threshold to detect circuit 34/54 for comparison to the digitized cardiac data provided on line 72 from AGC/filter and digitizing circuit 30/50. Detection circuit 34/54 provides a detection signal indicating R-wave or P-wave depolarizations representative of cardiac events when the value of the incoming digital cardiac data is greater than the sensing threshold level provided that the refractory windows are inactive. Template generation circuit 36/56 includes circuitry for selecting and adjusting the variable sensing threshold to a level proportional to the amplitude of the digital cardiac data on line 72. Typically, template generation circuit 36/56 responds very quickly to change the sensing threshold to the peak value of the digital cardiac data on line 72. The variable sensing threshold is held at the peak value for a selected period of time after which the variable sensing threshold drops to a percentage of the peak value. The variable sensing threshold is then allowed to slowly decay from this percentage of peak value in discrete steps until the variable sensing threshold is at a low threshold value. Template generation circuit 36/56 preferably employs integer math to achieve a piecewise linear approximation of a geometric progression such as an exponential decay curve with minimal error between piecewise steps.

Refractory Periods

Cardioverter/defibrillator 20 utilizes ventricular and atrial refractory periods to determine which sensed events are R-waves or P-waves respectively. The active sensed refractory periods are illustrated in timing diagram form on line 73 at 74 in FIG. 3. Any sensed event that occurs when the sensed refractory period is inactive is considered to be a R-wave or P-wave. Any events sensed during the active sensed refractory period are ignored and do not affect the ventricular or atrial cycle length measurement. Typical sensed events occurring on the lead are represented on line 75 at 76. As illustrated, the start of the active ventricular or atrial refractory period is synchronized with the start of the cardiac cycle. An absolute refractory interval is indicated on line 77 at 78. The absolute refractory interval starts at the beginning of the cardiac cycle simultaneous with the start of the active sensed refractory period. The absolute refractory interval disables all sensing. The operation of template generation circuit 36/56 based on the absolute refractory interval is further described below under the Threshold Templating for a Fast Digital AGC Circuit heading.

During pacing or shock delivery from cardioverter/defibrillator 20 a paced/shock refractory period, as indicated on line 79 at 81 in FIG. 4, is utilized instead of the sensed refractory period. Similar to the sensed refractory period, any sensed event that occurs when the paced/shock refractory period is inactive is considered to be a R-wave or P-wave. Typical pace pulses on the lead are represented for illustrative purposes on line 83 at 85. A typical shock pulse is not shown. The paced/shock refractory period is started with the delivery of the pace or shock pulse. Absolute refractory intervals are not utilized during pacing or shocking conditions. The time duration of the paced refractory period is preferably programmable, while the time duration of the shock refractory period is typically not programmable. The paced refractory period can be selected by the physician and programmed into cardioverter/defibrillator 20 when the cardioverter/defibrillator is operating in a pacing mode. The operation of template generation circuit 36/56 based on the paced/shock refractory period is further described below under the Threshold Templating for a Fast Digital AGC Circuit heading.

Slow Gain Control Circuit

Figure 5:
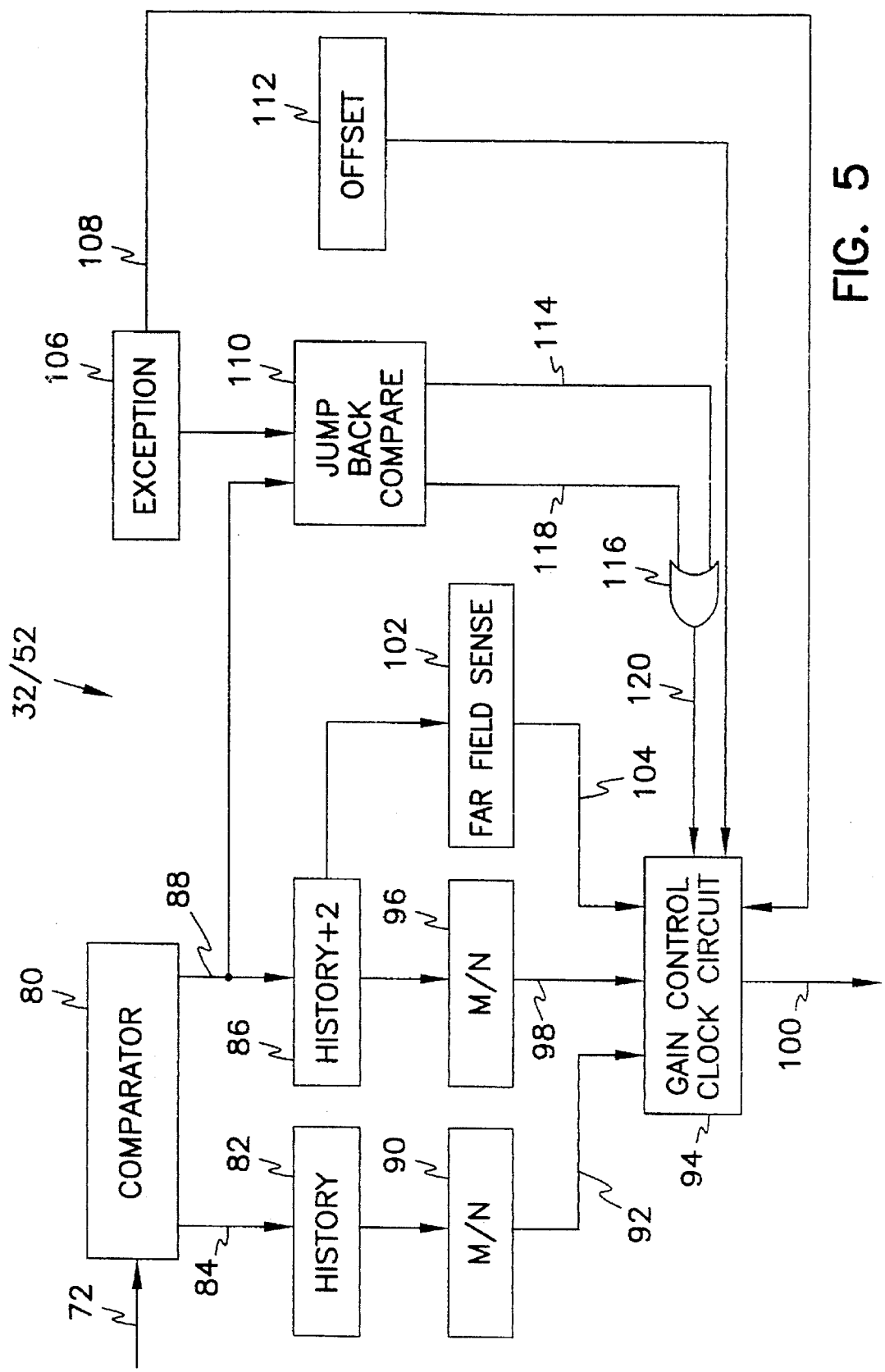
FIG. 5 is a logical block diagram of a gain control circuit according to the present invention.

Gain control circuit 32, or alternately gain control circuit 52, is representatively illustrated in FIG. 5 in logical block diagram form. A comparator 80 receives the digital cardiac data on line 72 and compares the peak value of the digital data representing the current cardiac event to a selected low threshold and a selected high threshold. For example, in one preferred embodiment of the present invention where the maximum value of the peak value of the digital cardiac data is 7F hex, the selected low threshold is 52 hex and the selected high threshold is 7E hex. A first storage register 82 includes a first group of storage locations which store peak history information provided by comparator 80 on a line 84 indicative of whether the peak values are below the selected low threshold (52 hex in the example embodiment). A second storage register 86 includes a second group of storage locations which store peak history information provided by comparator 80 on a line 88 indicative of whether the peak values are above the selected high threshold (7E hex in the example embodiment).

An M/N circuit 90 receives peak history information from storage register 82 and determines if M peak values of N cardiac events are below the selected low threshold (52 hex). M/N circuit 90 provides an increment signal on a line 92 to a gain control clock circuit 94. M/N circuit 90 activates the increment signal on line 92 when M out of N peak values are below the selected low threshold (52 hex) to indicate that the gain of AGC/filter and digitizing circuit 30/50 is to be incremented by at least one discrete gain step. In one embodiment of the present invention, the discrete gain step is approximately equal to 1.25. An M/N circuit 96 receives peak history information from storage register 86 and determines if M peak values of N cardiac events are above the selected high threshold (7E hex). M/N circuit 96 provides a decrement signal on a line 98 to gain control clock circuit 94. M/N circuit 96 activates the decrement signal on line 98 when M out of N peak values are above the selected high threshold (7E hex) to indicate that the gain of AGC/filter and digitizing circuit 30/50 is to be decremented by at least one discrete gain step. The decrementing discrete gain step is preferably equal to the incrementing discrete gain step and is approximately equal to 1.25 in one embodiment of the present invention.

Gain control clock circuit 94 provides a gain control signal on a line 100 which controls the gain of AGC/filter and digitizing circuit 30/50 by causing the gain to be incremented or decremented in discrete gain steps based on the increment signal on line 92 and the decrement signal on line 98. The gain of AGC/filter and digitizing circuit 30/50 can be increased or decreased by a fixed number of steps or amount, or the level of the discrete gain step is optionally made programmable via microprocessor and memory 38. In addition, gain control and clock circuit 94 optionally causes increments or decrements of gain in multiple discrete gain steps. Since the increment signal on line 92 and the decrement signal on line 98 are never activated at the same time due to the dual low threshold (52 hex) and high threshold (7E hex), no arbitration circuitry is necessary to arbitrate between the increment or decrement signals to indicate which direction to proceed. Gain control circuit 32/52 preferably keeps the peak values of atrial or ventricle sensed cardiac events in approximately the upper one third of the dynamic range of A/D converter 62. As a result, the lower approximately two thirds of the dynamic range of A/D converter 62 is available for sensing low amplitude signals such as occurring during fibrillation.

The above referenced number of M peak values is preferably odd to prevent lock-up of the AGC loop. For example, in a preferred embodiment of gain control circuit 32/52, M is equal to three and N is equal to four. In this embodiment, storage register 82 stores peak history information for four cardiac events in four corresponding storage locations each representative of whether the corresponding one of the last four values for peak values was below the selected low threshold (52 hex). In this embodiment, storage register 86 stores peak history information for four cardiac events in four corresponding storage locations each representative of whether the corresponding one of the last four values for peak values was above the selected high threshold (7E hex).

The peak values in storage register 82 and storage register 86 are preferably updated at the beginning of a new refractory period for a previous sensed event. As new peak value information is acquired from comparator 80, the old peak history information is shifted one value to the right. If storage registers 82 and 86 only contain four storage locations, the peak history values older than the last four cardiac events are shifted out of the registers to the right and lost.

In a preferred embodiment of the present invention, M/N circuit 90 activates the increment signal on line 92 only if the stored peak value of the last cardiac event and M-1 peak values of the last N-1 cardiac events previous to the last cardiac event are below the selected low threshold (52 hex). In this preferred embodiment of the present invention, M/N circuit 96 activates the decrement signal on line 98 only if the stored peak value of the last cardiac event and M-1 peak values of the last N-1 cardiac events previous to the last cardiac event are above the selected high threshold (7E hex).

Gain control circuit 32/52 operates as described above to minimize the possibility of improper sensing by not allowing AGC/filter and digitizing circuit 30/50 to go to low sensitivity if large R-waves or P-waves are present or to go to full sensitivity in the presence of slow R-waves or P-waves. Improper sensing can cause therapy to be delivered to a patient at inappropriate times as a result of false indications of arrhythmia conditions. Oversensing is reduced because the full sensitivity of AGC/filter and digitizing circuit 30/50 is not reached between slow beats as a result of gain control circuit 32/52 keeping the amplified depolarization electrical activity in the upper approximately one third of the dynamic range of A/D converter 62. The reduced oversensing greatly increases the comfort level of a patient having the cardioverter/defibrillator according to the present invention implanted in his or her body. Undersensing is reduced because minimum sensitivity will not occur due to a single large R-wave or P-wave.

In addition, as indicated above, gain control circuit 32/52 eliminates the need for a high precision A/D converter implementation of A/D converter 62, because the entire dynamic range of the incoming cardiac signal does not need to be spanned. Thus, in the preferred embodiment of the present invention, A/D converter 62 is implemented in 8 bits or less. The dynamic range of the incoming cardiac signal from the atrial and/or ventricular channels of the heart ranges from 0.1 mV to 25 mV representing a 250 to 1 dynamic range. Lower precision A/D converters consume less power, convert the incoming analog signal to representative digital data more quickly, and allow more cost effective silicon processes to be utilized. Moreover, manufacturability of the cardioverter/defibrillator is improved since no external parts are required to control the gain of the AGC/filter and digitizing circuit 30/50. Testing and characterization of the cardioverter/defibrillator is also improved since the digital logic of the gain control circuit 32/52 is easily fault graded.

AGC Turn Down Mechanism for Far Field Sensing

The preferred embodiment of gain control circuit 32/52 illustrated in FIG. 5 includes a far field sense circuit 102. Far field sense circuit 102 provides a solution to a possible AGC loop lock-up due to far field sensing. For example, when sensing events in the ventricle channel of the heart, P-waves, representing far field events, can be sensed during normal sinus rhythms at maximum sensitivity. Under this example condition, instead of AGCing on the R-wave peaks, which are clipped, the P-wave peak level alternating with the clipped R-wave peak level combine to inhibit gain changes. The clipped R-wave peaks indicate that the R-wave peaks are above the maximum digital value for a peak signal. In this case, the M of N algorithm is never met in M/N circuit 96, which causes a lock-up condition in the AGC loop. Far field sense circuit 102 provides an additional gain decrease option to gain control circuit 32/52 in addition to the normal modes of operation to prevent this lock-up condition from occurring.

In the embodiment illustrated in FIG. 5, two additional history storage locations are provided in storage register 86 to extend the peak history information to N+2 storage locations. Far field sense circuit 102 responds to the last N+2 sensed events stored in storage register 86 to determine if the storage information alternates between clipped peaks and non-clipped peaks for the last N+2 sensed events. Far field sense circuit 102 determines that a peak is clipped when the peak is at the maximum value (7F hex) which corresponds to peak values greater than the high threshold value used by comparator 80 (7E hex). Far field sense circuit 102 provides a decrement signal on a line 104 to gain control clock circuit 94. Far field sense circuit 102 activates the decrement signal on line 104 when the peak history information in storage register 86 alternates between clipped peaks and non-clipped peaks for the last N+2 sensed events. In one embodiment, the decrement signal on line 104 indicates that gain of AGC/filter and digitizing circuit 30/50 is to be decremented by one discrete gain step, but can alternatively indicate any number of discrete gain step changes.

Far field sense circuit 102 operates in the cases where the actual depolarization of the incoming cardiac signal is clipped to prevent the digital AGC loop from locking up under the condition of far field sensed events. If far field events are detected in the above manner, the gain of AGC/filter and digitizing circuit 30/50 is decreased to the point that far field events no longer are sensed. Previous cardioverter/defibrillator devices all oversense (double count) under this far field sensing condition. The far field sense circuit 102 according to the present invention greatly improves sensing discrimination by minimizing or substantially eliminating oversensing in the presence of far field events. Accordingly, the cardioverter/defibrillator according to the present invention provides a patient and his or her physician a cardioverter/defibrillator which senses the R-wave depolarizations more reliably.

Slow Gain Jump Back for AGC

Previous gain circuitry reaches maximum sensitivity in a single cardiac cycle. Unlike previous gain circuitry, the slow gain circuitry according to the present invention described above makes discrete step gain changes of one or more discrete gain step per cardiac depolarization cycle, so that full sensitivity of the AGC/filter and digitizing circuit 30/50 is not reached between cardiac depolarizations, which can cause undersensing of cardiac events. As illustrated in FIG. 5, additional circuitry is preferably added to gain control circuit 32/52 to prevent undersensing of cardiac events.

Exception circuitry 106 detects any one of three conditions which indicate that the gain of the AGC/filter and digitizing circuit 30/50 is to be set to a selected relatively high sensitivity. Exception circuitry 106 provides a set gain signal on a line 108 to cause the gain of AGC/filter and digitizing circuit 30/50 to be set to the selected relatively high sensitivity when any of the three conditions occur. The first condition occurs when a cardiac event is not detected for a selected time period (i.e., a R-wave or P-wave depolarization is not sensed for the selected time period). Typically, the selected time period is equal to approximately 1.5 seconds, corresponding to a heart rate of less than 40 beats per minute. The second condition occurs after the cardioverter/defibrillator delivers a shock pulse. The third condition occurs after the cardioverter/defibrillator delivers a pacing pulse.

In any of the three conditions, it is desirable to prevent undersensing by setting the gain of the AGC/filter and digitizing circuit 30/50 to the selected relatively high sensitivity to quickly increase the sensitivity of the cardioverter/defibrillator. A/D converter 62 (Shown in FIG. 2) typically operates in bands of an approximately 10:1 dynamic range. The combined 10:1 dynamic range bands create a total 250:1 dynamic range of A/D converter 62. The three exception conditions are conditions where A/D converter 62 needs to operate near maximum sensitivity, or in other words, near the upper portion of the highest 10:1 dynamic range band to adequately prevent undersensing.

In the preferred embodiment of the present invention, the selected relatively high sensitivity is two gain steps from a maximum sensitivity to prevent mistaking P-wave depolarizations and T-wave repolarizations for R-wave depolarizations. If the selected relatively high sensitivity creates a clipped signal on the following depolarization, having its peak at the maximum value (7F hex), as indicated from comparator 80 on line 88, a jump back compare circuit 110 activates a line 114 to a two input OR gate 116 to indicate that the gain is to be reduced by an offset value stored in offset register 112. OR gate 116 provides a decrement signal on an enable line 120 to gain control clock circuit 94 which is activated when either of the two inputs to the OR gate are activated to indicate that the gain of AGC/filter and digitizing circuit 30/50 is to be decremented by at least one discrete gain step during the current refractory period. The offset value stored in register 112 is preferably programmable and is provided to gain control clock circuit 94. In one embodiment, the offset value is programmed to equal three discrete gain steps.

If the peak value of the digital cardiac data on line 72 is still clipped on the next depolarization after the gain has been decreased by the offset value stored in offset register 112, comparator 80 indicates on line 88 that the peak of the cardiac signal is still clipped. Jump back compare circuit 110 then indicates that the gain is to be decremented by at least one discrete gain step by activating a line 118 to the other input of OR gate 116, which correspondingly activates enable line 120 to gain control clock circuit 94. If the peak value is still clipped, normal AGC action as described above resumes. This two staged back off mechanism after a jump out or escape to the selected relatively high sensitivity due to lack of sensing reduces oversensing resulting from the clipped peak of the cardiac signal.

If the peak value of the digital cardiac data on line 72 is not clipped on the first depolarization after the gain is set to the relatively high sensitivity, but the peak value is clipped on the second depolarization after the gain is set to the relatively high sensitivity by having its peak at the maximum value (7F hex), as indicated from comparator 80 on line 88, jump back compare circuit 110 activates line 114 to two input OR gate 116 to indicate that the gain is to be reduced by the offset value stored in offset register 112. OR gate 116 provides the decrement signal on enable line 120 to gain control clock circuit 94 which is activated when either of the two inputs to the OR gate are activated to indicate that the gain of AGC/filter and digitizing circuit 30/50 is to be decremented by at least one discrete gain step during the current refractory period. If the peak value is still clipped, normal AGC action as described above resumes. This situation, where the peak value of the first detected depolarization is not clipped and the peak value of the second detected depolarization is clipped after the gain is set to the relatively high sensitivity, results when the first depolarization represents a far field sensed event such as described above. For example, when sensing events in the ventricle channel of the heart, P-waves, representing far field events, can be sensed during normal sinus rhythms at maximum sensitivity.

Threshold Templating for a Fast Digital AGC Circuit

Figure 6:
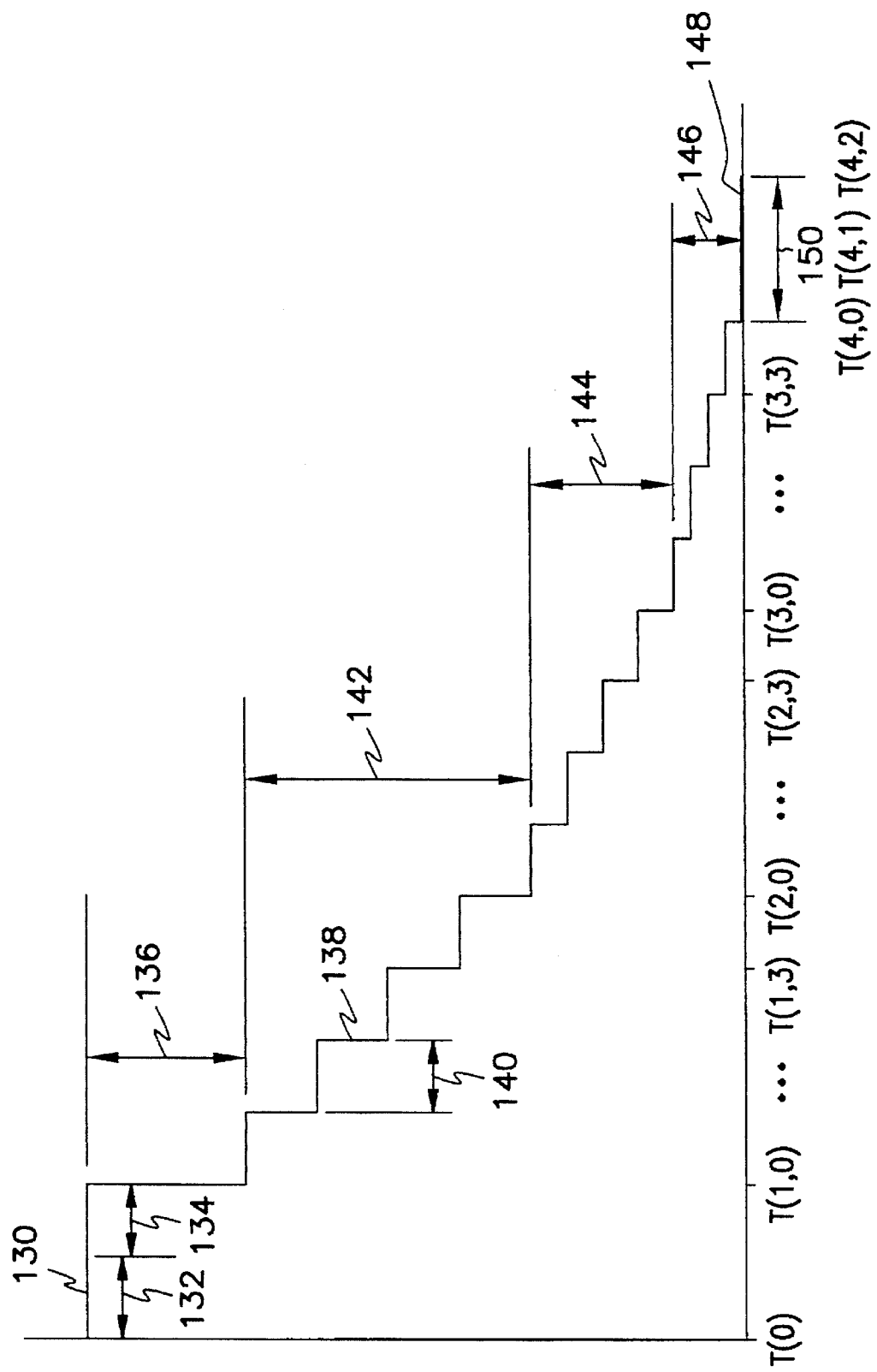
FIG. 6 is a timing diagram illustrating a piecewise linear approximation of an exponential decay of the variable sensing threshold according to the present invention.

FIG. 6 illustrates, in timing diagram form, the variable sensing threshold generated by template generation circuit 36/56 and provided to detection circuit 34/54. The variable sensing threshold is indicated by line 130. As illustrated, the variable sensing threshold 130 follows a piecewise linear approximation of an exponential decay curve with minimal error between steps. The template generation circuit 36/56 forces the variable sensing threshold 130 to rapidly follow the maximum peak level of the digitized cardiac data. When the incoming digitized cardiac data is greater than the current sensing threshold, template generation circuit 36/56 raises the variable sensing threshold 130 to a peak threshold value approximately equal to the peak value of the incoming digitized cardiac data as indicated at time T(0). After a shock or pace pulse is delivered by the cardioverter/defibrillator, template generation circuit 36/56 sets the variable sensing threshold 130 to a selected relatively high threshold value. The selected relatively high threshold value is preferably 7E hex in the example embodiment or one binary number below the maximum value of the variable threshold.

The variable sensing threshold 130 remains at the peak threshold value through a refractory or a portion of a refractory period indicated at 132. When the cardioverter/defibrillator is operating in pacing mode, the period indicated at 132 is a programmed paced refractory period that is selected by the physician and programmed into the cardioverter/defibrillator, such as the paced/shock refractory period indicated at 81 is FIG. 4. When the cardioverter/defibrillator is operating in shocking mode, the period indicated at 132 is a shock refractory period, such as the paced refractory period indicated at 81 is FIG. 4. When the cardioverter/defibrillator is operating in sensing mode, the period indicated at 132 is a portion of a sensed refractory period, such as the absolute refractory period indicated at 78 is FIG. 4. In addition to the refractory or the portion of a refractory period indicated at 132, the variable sensing threshold does not begin to decay from the peak threshold value attained at time T(0) for an additional drop time indicated at 134. The drop time is a normal template hold time for the peak converter circuitry of template generation circuit 36/56, and is empirically determined. A suitable value for the drop time in one embodiment of the present invention is approximately 13.7 msec.

After the refractory period and the drop time have elapsed, at time T(1,0) the variable sensing threshold 130 drops by an initial drop percentage, indicated by arrows 136. The initial drop percentage is preferably approximately 25% of the peak threshold value so that the level of the variable sensing threshold obtained at time T(1,0) is approximately 75% of the initial peak threshold value. As indicated at time T(1,1), the variable sensing threshold starts to decay in discrete steps such as indicated at 138. The step time size is representatively indicated by arrows 140 between time T(1,1) and T(1,2). The level of the variable sensing threshold 130 decays from a percentage of the peak threshold value to step over wide depolarizations or T-waves in the incoming electrical activity.

In the preferred embodiment of the present invention, template generation circuit 36/56 drops the variable sensing threshold 130 in step groups comprising multiple discrete steps. In the embodiment illustrated in FIG. 6, the step group size is four. Each step group decreases the variable sensing threshold by a defined percentage, as indicated by arrows 142 for a four step group between time T(1,0) and T(2,0), arrows 144 for a four step group between T(2,0) and T(3,0), and arrows 146 for a four step group between T(3,0) and T(4,0). The defined percentage for each step group is preferably approximately 50%. For example, in the preferred embodiment of the present invention, the value of the variable sensing threshold at time T(2,0) is approximately 50% of the value of the variable sensing threshold at time T(1,0), and the value of the variable sensing threshold at time T(3,0) is approximately 50% of the value of the variable sensing threshold at time T(2,0) or 25% of the value of the variable sensing threshold at time T(1,0).

When the variable sensing threshold 130 decays to a programmable final value, as indicated at 148, template generation circuit 36/56 holds the variable sensing threshold at the programmable final value until a new sensed event occurs. The programmable final value is programmable to compensate for noise which is inherent in the sense amplifiers and other AGC system circuits of the AGC loop.

The initial drop percentage to achieve approximately 75% of the peak threshold value, and the four discrete steps in each step group to drop the variable sensing threshold to approximately 50% of the level of the start of the four-step group realizes a piecewise geometric progression linear approximation representing an exponential decay curve with minimal error between piecewise steps. Since the sensing threshold drops in discrete steps as indicated at 138, integer math can be utilized in template generation circuit 36/56. For example in the embodiment of template generation circuit 36/56 illustrated in FIG. 6, floating point numbers are not required because the maximum difference/error between any two discrete steps in a four step group is one bit. The present invention can be extended to use any size integer value or number of steps or step groups to achieve the linear approximation of the exponential decay curve. In fact, floating point numbers are optionally used, but are not desirable because of the increased silicon area needed to implement floating point logic circuits. In addition, by implementing the template generation circuit with integer values, the resulting template generation circuit consumes a relatively small amount of power.

A preferred algorithm for calculating the drop in amplitude for each of the discrete steps is shown in TABLE I below.

TABLE I

| INTER-VAL | STEP CALCULATION |
|---|---|
| T(X,0) | TEMP = T(0) − T(0) /2 + T(0) /4<br>TEMP1 = T(X−1,0) /2<br>= IF (X = 1) THEN<br>   IF (FINAL THRESHOLD > TEMP) THEN FINAL<br>   ELSE TEMP<br>ELSE<br>   IF (FINAL THRESHOLD > TEMP1) THEN FINAL<br>   ELSE TEMP1 |
| T(X,1) | TEMP = T(X,0) − T(X,0) /4 + T(X,0) /8<br>= IF (FINAL THRESHOLD > TEMP) THEN FINAL<br>ELSE TEMP |
| T(X,2) | TEMP = T(X,0) − T(X,0) /2 + T(X,0) /4<br>= IF (FINAL THRESHOLD > TEMP) THEN FINAL<br>ELSE TEMP |
| T(X,3) | TEMP = T(X,0) − T(X,0) /2 + T(X,0) /8<br>= IF (FINAL THRESHOLD > TEMP) THEN FINAL<br>ELSE TEMP |
| Where: | |
| T0 | = PEAK THRESHOLD VALUE |
| T(X,1...3) | = One of Four Steps |
| X | = 1,2,3,4 - Decay Period |

Referring to TABLE I above, in the interval T(X,0), TEMP is calculated to 75% of the initial peak threshold value, and TEMP1 is calculated to 50% of a previous step group value. If the step group is the first drop from the peak threshold value, then T(1,0) is equal to TEMP or 75% of the peak value. In successive drops, T(X,0) is equal to TEMP1 or a 50% drop from the level at the beginning of the previous step group.

In all of the T(X,1), T(X,2), and T(X,3) intervals, the variable sensing threshold obtains the TEMP value unless the TEMP value is less than FINAL THRESHOLD which is the final programmable value indicated at 148 in FIG. 6. For example, in the T(X,1) interval, T(X,1) is set to TEMP which is calculated to 87.5% of the T(X,0) value. In the T(X,2) interval, T(X,2) is set to TEMP which is calculated to 75% of the T(X,0) value. In the T(X,3) interval, T(X,3) is set to TEMP which is calculated to 62.5% of the T(X,0) value.

A logical block diagram of a preferred embodiment of template generation circuit 36/56, which uses integer values for calculating the variable sensing threshold, is illustrated in FIG. 7. A peak detection circuit 160 detects the peak value of the digitized cardiac data provided on line 72 from AGC/filter and digitizing circuit 30/50. Peak detection circuit 160 provides a peak threshold value which is equal to the peak value of the digitized data to a threshold register 162 if the digitized peak is greater than the current threshold value. Threshold register 162 stores and provides the current variable sensing threshold on line 164 to the detection circuit 34/54. Peak detection circuit 160 also provides the peak threshold value to T(X,0) register 166.

If the step group is not the first drop from the peak threshold value the TEMP1 calculation must be implemented for the T(X,0) interval of the discrete step calculation algorithm in TABLE I above. To implement the TEMP1 calculation, the T(X-1,0) value stored in the T(X,0) register 166 from the previous step group is divided by 2 through a hard shift of one to the right as indicated by line 168 to place the shifted data in both the threshold register 162 and the T(X,0) register 166.

T(X,0) register 166 provides its currently stored value to a subtraction circuit 170 and a shifter 172. Shifter 172 provides either a divide by 2 or a divide by 4 calculation by shifting the current T(X,0) value by one bit or two bits to the right, respectively. Subtractor 170 subtracts the value stored in the T(X,0) register 166 from a shifted output provided from shifter 172. The shifted output of shifter 162 is also provided to a shifter 174. Shifter 174 provides an additional divide by 2 or divide by 4 through shifts of 1 bit or 2 bits to the right, respectively. A difference output of subtractor 170 is provided to an adder 176. A shifted output of shifter 174 is provided to the other input of adder 176. Adder 176 adds the difference output of subtractor 170 and the shifted output of shifter 174 and provides the added value to threshold register 162.

The shifters 172 and 174 can, in combination, achieve shifts of 1, 2, 3, or 4 bits to produce divide by 2, divide by 4, divide by 8, or divide by 16 calculations. The TEMP calculations required for the T(X,0), T(X,1), T(X,2), and T(X,3) intervals of the discrete step calculation algorithm in TABLE I above are all achieved through shifters 172 and 174 in combination with subtractor 170 and adder 176. Shifters 172 and 174 calculate the desired divide by values which are then properly combined according to the algorithm in TABLE I with subtractor 170 and adder 176.

A final threshold register 178 stores the programmable final value, indicated at 148 in FIG. 6, of the variable sensing threshold. The programmable final value is provided to a threshold comparator 180. Threshold comparator 180 compares the programmable final value stored in final threshold register 178 with the current variable sensing threshold value on line 164. Threshold comparator 180 indicates to threshold register 162, on a line 182, whether the current variable sensing threshold value is greater than the programmable final value. If the programmable final value is greater than the calculated sensing threshold value, then the final value is stored in threshold register 162. The sensing threshold value stays at the final value until the incoming digitized cardiac data exceeds the final value indicating a new sensed event. In fact, a new sensed event occurs any time the incoming digitized cardiac data peak value exceeds the current variable sensing threshold value on line 164. With the new sensed event, the variable sensing threshold obtains a new T(0) peak threshold value equal to the peak value of the sensed depolarization in the digitized cardiac data.

The above described threshold templating algorithm for a fast digital AGC system is completely contained in digital logic as implemented in the preferred embodiment. The digital logic implementation is easily characterized, tested, and achieves repeatable results. In addition, external parts are eliminated from the silicon chip implementation of the AGC circuitry to reduce cost and increase the manufacturability of the AGC silicon chip. Testing and characterization of the cardioverter/defibrillator devices is uniform from one device to another. In this way, it is easier for the physician to determine how to implement the cardioverter/defibrillator device in a patient, because the device reacts consistently from one unit to another.

Tailorable AGC Decay Rate

No single decay rate (attack rate) is optimal for all operating conditions of a cardioverter/defibrillator with pacing capability for the above described fast response AGC circuit. The typical operating conditions encountered include bradycardia pacing, tachyrhythmia sensing, and normal sinus sensing. Therefore, according to the present invention, the step time size indicated by arrows 140 in FIG. 6 is programmable to achieve a tailorable AGC decay rate for the variable sensing threshold 130. In this way, by varying the step time size 140 for each of the defibrillator's operating conditions, the decay rate is customized to optimally meet the selected operating condition.

For normal sinus sensing, a single attack rate is utilized that covers most of the incoming cardiac signals. In one embodiment of the present invention, the step time size 140 is set to 29.3 mSec/step to achieve the normal sinus sensing decay rate.

Tachyrhythmia sensing is a special condition under which a fast response rate is desirable in order to properly track the higher tachyrhythmia rates, such as during fibrillation or tachycardia. This is especially true in the atrium of the heart, where tachyrhythmia rates run in excess of 300 beats per minute. In one embodiment of the present invention, step size 140 is set to approximately 17.5 mSec/step for atrial tachyrhythmia conditions, and is set to approximately 23.5 mSec/step for ventricle tachyrhythmia conditions. By switching to this faster decay rate for tachyrhythmia conditions, cases of undersensing a tachyrhythmia condition which needs to be treated is reduced.

Bradycardia pacing is a special operating condition wherein the decay rate of the sensing threshold is tied to the bradycardia pacing rate to help minimize oversensing and undersensing conditions. In prior cardioverter/defibrillator devices with pacing capability, the sensing template attack rate is fixed. Under situations of high pacing rates, the cardioverter/defibrillator with pacing capability utilizing AGC according to the present invention does not have time to decay to maximum sensitivity. If the decay rate is not sufficiently sped up along with the high pacing rates undersensing occurs and the cardioverter/defibrillator continues pacing in the presence of fibrillation. With the decay rate varied as a function of the bradycardia pacing rate under bradycardia pacing conditions, the decay rate is sufficiently sped up to enable the cardioverter/defibrillator according to the present invention to sense and properly respond to the fibrillation condition. In addition, when pacing rates are low, a longer decay rate is desirable to minimize the possibility of oversensing.

The formula for calculating the post pace template step time size 140 for bradycardia pacing conditions is as follows:

STEP TIME SIZE=(CYCLE LENGTH— REFRACTORY—DROP TIME—MINIMUM TIME)/X where:

| | |
|---|---|
| CYCLE LENGTH | = pacing cycle length |
| REFRACTORY | = programmed paced refractory |
| DROP TIME | = normal template hold time for peak converter (approximately 13.7 mSec in a preferred embodiment) |
| MINIMUM TIME | = minimum time allowed for template at final value (approximately 100 mSec in a preferred embodiment) |
| X | = number of steps to go from seed value to final value (equal to 12 steps in the embodiment illustrated in FIG. 6) |

Referring to FIG. 6, the cycle length is equal to the pacing cycle length or from time T(0) to T(0) between each pacing pulse. The paced refractory period is indicated by arrows 132. The drop time is indicated by arrows 134. The time the variable sensing threshold is at the programmable final value before the next pacing pulse is indicated by arrows 150. Since multiple pacing rates are assigned the same step size, the time indicated at 150 varies from approximately 100 mSec to 200 mSec in the embodiment illustrated. The minimum time is the minimum time allowed for the time indicated by arrows 150, or approximately 100 mSec. X represents the 12 steps (i.e., the 3 X four step groups) to go from the peak sensing value at time T(0) to the programmed final value of the variable sensing threshold achieved at T(4,0).

A look-up table stored in microprocessor and memory 38 is formed by dividing the cycle length by 64, which results in a shift of six bits to the right. In one implementation of the present invention, the cycle length is equal to 12 bits, which results in six bits being shifted off in the divide by 64 formation of the look-up table in microprocessor and memory 38, resulting in 64 entries in the look-up table. Thus, the current cycle length is divided by 64 to index the look-up table to access the values stored in the look-up table corresponding to the above step time size formula.

The digital embodiment of the AGC loop as described above allows the above described firmware implemented in the look-up table in the microprocessor and memory 38 to dynamically adjust the sensing characteristics of the cardioverter/defibrillator according to the present invention. By sensing high rates differently than low rates, the tailorable AGC decay rate according to the present invention can be utilized to orthogonally optimize sensing characteristics of bradycardia and tachyrhythmia signals, which have mutually exclusive sensing requirements. In this way, the physician controls a better-behaved cardioverter/defibrillator. In addition, patient comfort is increased, due to reducing oversensing and undersensing of treatable arrhythmia conditions in the patient.

Interaction of Digital AGC Using Separate Gain Control and Threshold Templating

Figure 8:
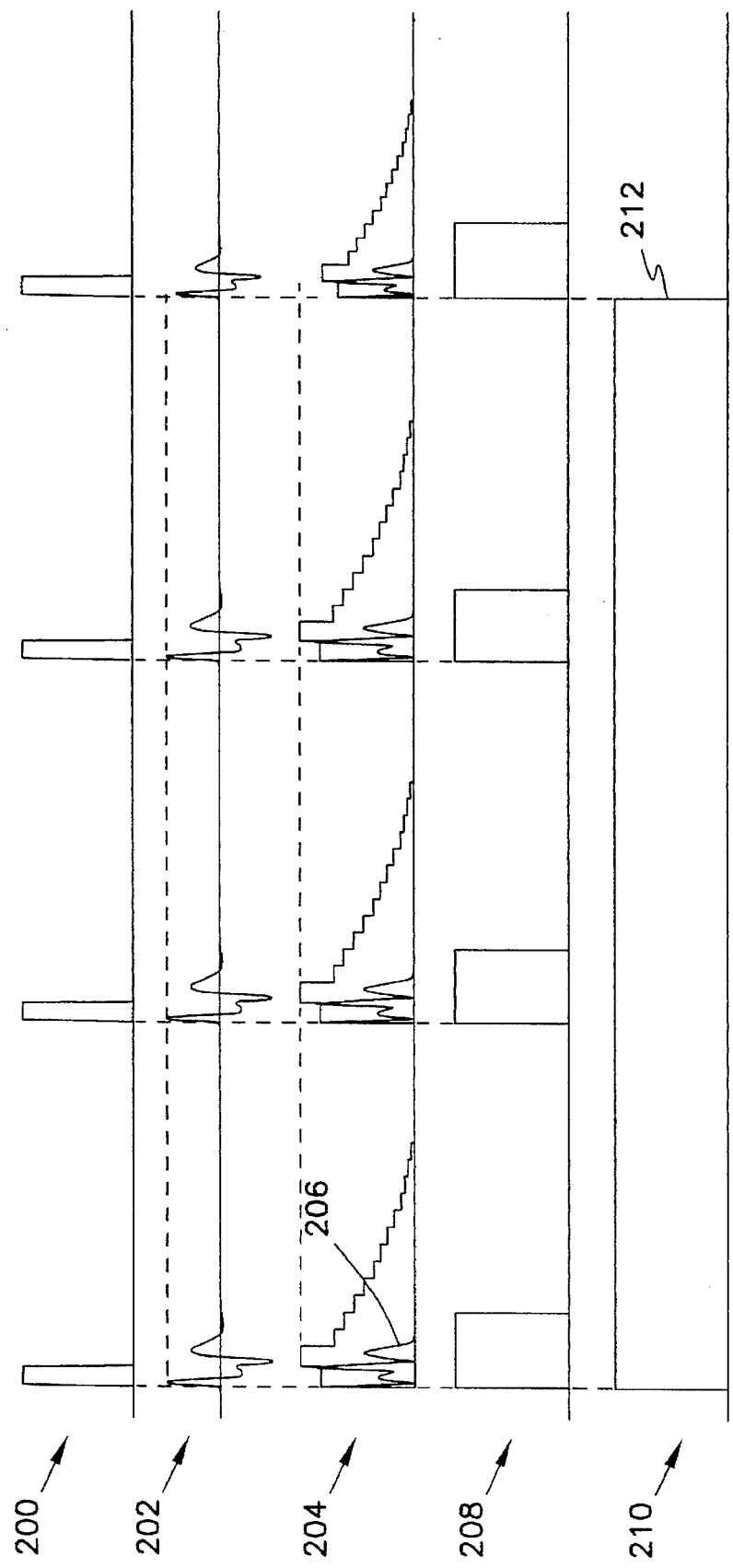
FIG. 8 is a timing diagram illustrating the operation of the slow gain control circuit of FIG. 5, in combination with the fast templating generation circuit of FIG. 7 in adjusting the gain and the sensing threshold of the cardioverter/defibrillator according to the present invention.

FIG. 8 illustrates in timing diagram form depolarization cycles in the electrical activity of the heart. The incoming electrical activity at input/output terminals 22 or 42 is indicated by waveform 200. The filtered and gain controlled digitized cardiac signal is indicated by waveform 202. The variable sensing threshold is indicated by waveform 204. The absolute value of the digitized and gain controlled cardiac signal is indicated by waveform 206 underneath the variable sensing threshold waveform 204. The refractory period is indicated by waveform 208. The discrete stepped slow gain is indicated by waveform 210.

As indicated by waveform 204, the variable sensing threshold waveform responds to the absolute value of the digitized cardiac signal to assume the peak value of the digitized cardiac signal. The variable sensing threshold then decays according to a piecewise linear approximation of an exponential decay curve to step over wide depolarizations or T-waves.

The influence of the slow gain control on the fast templating circuit is illustrated at time 212. As is indicated, the gain is decreased at time 212, which correspondingly results in a reduced filtered and gain controlled digitized cardiac signal indicated at 202, which correspondingly reduces the variable sensing threshold indicated at 204 as the variable sensing threshold follows the peak value of the absolute value of the digitized and gain controlled cardiac signal indicated at 206.

Conclusion

By utilizing this present invention, which incorporates two independent loops in a cardioverter defibrillator with pacing capability which are both implementing digital logic circuits, the AGC response is effectively moved from analog circuits into the digital logic circuits, where it is easier to test and characterize. Design of the sense amplifier is simplified, due to the digital control of the sense amplifier. It is easier to test and characterize the analog sense amplifier, since the AGC circuitry is no longer in the analog domain. The cardioverter/defibrillator device is more uniform from device to device, which greatly increases the physician's ease of predicting device behavior. In addition, the patient comfort is increased due to reduced oversensing and undersensing.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What we claim is:

1. A method of automatically controlling a gain of a cardioverter/defibrillator which receives electrical activity of the heart and provides shock pulses in response thereto, the method comprising the steps of:

amplifying the electrical activity according to a variable gain;

detecting cardiac events representing depolarizations in the amplified electrical activity which exceed a sensitivity threshold; and increasing the variable gain if a first selected number (M) of peak values of the amplified electrical activity of a second selected number (N) of cardiac events are below a selected low threshold, wherein M is an odd integer number equal to or greater than 3 and N is an integer number equal to or greater than M; and decreasing the variable gain if M peak values of the amplified electrical activity of the N cardiac events are above a selected high threshold.

2. The method of claim 1 wherein variable gain is increased in the increasing step if a stored peak value of the last cardiac event and M-1 peak values of the last N-1 cardiac events previous to the last cardiac event are below the selected low threshold and the variable gain is decreased in the decreasing step if the stored peak value of the last cardiac event and M-1 peak values of the last N-1 cardiac events previous to the last cardiac event are above the selected high threshold.

3. The method of claim 1 wherein M is at least 3 and N is at least 4.

4. The method of claim 1 further comprising the step of setting the gain to a selected relatively high sensitivity based on a certain condition occurring.

5. The method of claim 4 wherein the certain condition occurs when a cardiac event is not detected within a selected time period.

6. The method of claim 4 wherein the certain condition is a shock pulse being delivered by the cardioverter/defibrillator.

7. The method of claim 4 wherein the method automatically controls the gain of a cardioverter/defibrillator having pacing capability, and wherein the certain condition is a pacing pulse being delivered by the cardioverter/defibrillator.

8. The method of claim 4 wherein the steps of increasing and decreasing the variable gain are performed in discrete steps and the selected relatively high sensitivity is at least one discrete step from a maximum sensitivity.

9. The method of claim 8 further comprising the step of decrementing the gain from the selected relatively high sensitivity by a selected number of discrete gain steps if the setting of the gain to the selected relatively high sensitivity creates a clipped peak value of the amplified electrical activity on the following detected cardiac event.

10. The method of claim 9 further comprising the step of further decrementing the gain by at least one discrete gain step if the peak value of the amplified electrical activity is still clipped on the second detected cardiac event following the setting of the gain to the selected relatively high sensitivity.

11. The method of claim 8 further comprising the step of decrementing the gain from the selected relatively high sensitivity by a selected number of discrete gain steps if the setting of the gain to the selected relatively high sensitivity does not create a clipped peak value of the amplified electrical activity on the following detected cardiac event and does create a clipped peak value of the amplified electrical activity on the second detected cardiac event following the setting of the gain to the selected relatively high sensitivity.

12. The method of claim 1 further comprising the step of decreasing the variable gain if the peak values of the amplified electrical activity of a third selected number of cardiac events alternate between clipped peak values and non-clipped peak values.

13. The method of claim 12 wherein the third selected number is at least two more than N.

14. A system for automatically controlling a gain of a cardioverter/defibrillator, which receives electrical activity of the heart and provides shock pulses in response thereto, the system comprising:

an amplifier for amplifying the electrical activity of the heart according to a variable gain;

a cardiac depolarization detector for detecting depolarizations in the amplified electrical activity of the heart and providing a detect signal representing a cardiac event indicative of a depolarization when the amplified electrical activity exceeds a sensitivity threshold;

storage means for storing peak history information representative of peak values of the amplified electrical activity of a first selected number (N) of cardiac events; and gain controller for adjusting the variable gain in discrete steps based on the stored peak history information by increasing the variable gain by at least one discrete step if a second selected number (M) of peak values of the N cardiac events are below a selected low threshold and by decreasing the variable gain by at least one discrete step if M peak values of the N cardiac events are above a selected high threshold, wherein M is an odd integer number equal to or greater than 3 and N is an integer number equal to or greater than M.

15. The system of claim 14 wherein the gain controller increases the variable gain if a stored peak value of the last cardiac event and M-1 peak values of the last N-1 cardiac events previous to the last cardiac event are below the selected low threshold and decreases the variable gain if the stored peak value of the last cardiac event and M-1 peak values of the last N-1 cardiac events previous to the last cardiac event are above the selected high threshold.

16. The system of claim 14 wherein the storage means comprises a first group of storage locations which store peak history information indicating if the peak values are below the selected low threshold and a second group of storage locations which store peak history information indicating if the peak values are above the selected high threshold.

17. The system of claim 14 wherein M is at least 3 and N is at least 4.

18. The system of claim 14 wherein the peak history information from the previous cardiac event is updated at the beginning of a new refractory period caused by a cardiac event.

19. The system of claim 14 wherein the gain controller includes means responsive to the detect signal to set the gain to a selected relatively high sensitivity based on a certain condition occurring.

20. The system of claim 19 wherein the certain condition occurs when a cardiac event is not detected within a selected time period.

21. The system of claim 19 wherein the certain condition is a shock pulse being delivered by the cardioverter/defibrillator.

22. The system of claim 19 wherein the system automatically controls the gain of a cardioverter/defibrillator having pacing capability, and wherein the certain condition is a pacing pulse being delivered by the cardioverter/defibrillator.

23. The system of claim 19 wherein the gain controller adjusts the variable gain in discrete gain steps and the selected relatively high sensitivity is at least one discrete step from a maximum sensitivity.

24. The system of claim 23 further comprising means for decrementing the gain from the selected relatively high sensitivity by a selected number of discrete gain steps if the setting of the gain to the selected relatively high sensitivity creates a clipped peak value of the amplified electrical activity on the following detected cardiac event.

25. The system of claim 24 further comprising means for decrementing the gain by at least one discrete gain step if the peak value of the amplified electrical activity is still clipped on the second detected cardiac event following the setting of the gain to the selected relatively high sensitivity.

26. The system of claim 23 further comprising means for decrementing the gain from the selected relatively high sensitivity by a selected number of discrete gain steps if the setting of the gain to the selected relatively high sensitivity does not create a clipped peak value of the amplified electrical activity on the following detected cardiac event and does create a clipped peak value of the amplified electrical activity on the second detected cardiac event following the setting of the gain to the selected relatively high sensitivity.

27. The system of claim 14 wherein the storage means is capable of storing peak history information representative of peak values of the amplified electrical activity of a second selected number of cardiac events, and the system further comprises:

gain turndown means responsive to the stored peak history information to decrease the variable gain by at least one discrete step if the peak values of the amplified electrical activity of the second selected number of cardiac events alternate between clipped peak values and non-clipped peak values.

28. The system of claim 27 wherein the second selected number is at least two more than N.

29. A method for automatically controlling a gain of a cardioverter/defibrillator, which receives electrical activity of the heart and provides shock pulses in response thereto, the method comprising the steps of:

amplifying the electrical activity of the heart according to a variable gain;

detecting cardiac events representing depolarizations in the electrical activity which exceed a sensitivity threshold;

storing peak history information representative of peak values of the amplified electrical activity;

adjusting the variable gain in discrete steps based on the stored peak history information; and decreasing the variable gain by at least one discrete step in response to the stored peak history information if the peak values of the amplified electrical activity of a first selected number of cardiac events alternate between clipped peak values and non-clipped peak values.

30. The method of claim 29 wherein the adjusting step adjusts the variable gain based on the stored peak history information of a second selected number of cardiac events, and wherein the first selected number is at least two more than the second selected number.

31. The method of claim 29 wherein the adjusting step included the steps of increasing the variable gain by at least one discrete step if a third selected number of peak values of the second selected number of cardiac events are below a selected low threshold and decreasing the variable gain by at least one discrete step if the third selected number of peak values of the second selected number of cardiac events are above a selected high threshold.

32. The method of claim 31 wherein the first selected number is at least 6, the second selected number at least 4, and the third selected number is at least 3.

33. The method of claim 29 further comprising the steps of:

digitizing the amplified electrical activity; and comparing the digitized amplified electrical activity to a maximum peak digital value and indicating that a peak value is clipped when the peak value of the digitized amplified electrical activity is equal to the maximum peak digital value.

34. A system for automatically controlling a gain of a cardioverter/defibrillator, which receives electrical activity of the heart and provides shock pulses in response thereto, the system comprising:

amplifier for amplifying the electrical activity of the heart according to a variable gain;

a cardiac depolarization detector for detecting depolarizations in the amplified electrical activity of the heart and providing a detect signal representing a cardiac event indicative of a depolarization when the amplified electrical activity exceeds a sensitivity threshold;

storage means for storing peak history information representative of peak values of the amplified electrical activity;

gain control means for adjusting the variable gain in discrete steps based on the stored peak history information; and gain turndown means responsive to the stored peak history information to decrease the variable gain by at least one discrete step if the peak values of the amplified electrical activity of a first selected number of cardiac events alternate between clipped peak values and non-clipped peak values.

35. The system of claim 34 wherein the gain control means adjusts the variable gain based on the stored peak history information of a second selected number of cardiac events, and wherein the first selected number is at least two more than the second selected number.

36. The system of claim 35 wherein the gain control means increases the variable gain by at least one discrete step if a third selected number of peak values of the second selected number of cardiac events are below a selected low threshold and decreases the variable gain by at least one discrete step if the third selected number of peak values of the second selected number of cardiac events are above a selected high threshold.

37. The system of claim 36 wherein the first selected number is at least 6, the second selected number at least 4, and the third selected number is at least 3.

38. The system of claim 34 further comprising:

a analog to digital converter to digitize the amplified electrical activity; and a comparator for comparing the digitized amplified electrical activity to a maximum peak digital value and indicating that a peak value is clipped when the peak value of the digitized amplified electrical activity is equal to the maximum peak digital value.

39. A method for automatically controlling a gain of a cardioverter/defibrillator, which receives electrical activity of the heart and provides shock pulses in response thereto, the method comprising the steps of:

amplifying the electrical activity of the heart according to a variable gain;

detecting cardiac events representing depolarizations in the electrical activity which exceed a sensitivity threshold;

storing history information representative of the amplified electrical activity of a selected number of cardiac events;

adjusting the variable gain in discrete steps based the stored history information; and setting the variable gain to a selected relatively high sensitivity based on a certain condition occurring which substantially invalidates the history information.

40. The method of claim 39 wherein the certain condition occurs when a cardiac event is not detected within a selected time period.

41. The method of claim 39 wherein the certain condition is a shock pulse being delivered by the cardioverter/defibrillator.

42. The method of claim 39 wherein the method automatically controls a gain of a cardioverter/defibrillator having pacing capability, and wherein the certain condition is a pacing pulse being delivered by the cardioverter/defibrillator.

43. The method of claim 39 wherein the step of adjusting the variable gain is performed in discrete steps and the selected relatively high sensitivity is at least one discrete step from a maximum sensitivity.

44. The method of claim 43 further comprising the step of decrementing the gain from the selected relatively high sensitivity by a selected number of discrete gain steps if the setting of the gain to the selected relatively high sensitivity creates a clipped peak value of the amplified electrical activity on the following detected cardiac event.

45. The method of claim 44 further comprising the step of further decrementing the gain by at least one discrete gain step if the peak value of the amplified electrical activity is still clipped on the second detected cardiac event following the setting of the gain to the selected relatively high sensitivity.

46. The method of claim 43 further comprising the step of decrementing the gain from the selected relatively high sensitivity by a selected number of discrete gain steps if the setting of the gain to the selected relatively high sensitivity does not create a clipped peak value of the amplified electrical activity on the following detected cardiac event and does create a clipped peak value of the amplified electrical activity on the second detected cardiac event following the setting of the gain to the selected relatively high sensitivity.

47. The method of claim 40 wherein the selected time period is approximately 1.5 seconds.

48. The method of claim 39 wherein the adjusting step comprises the steps of:

storing peak history information representative of peak values of the amplified electrical activity of a first selected number (N) of cardiac events; and adjusting the variable gain based on the stored peak history information.

49. The method of claim 39 wherein the adjusting step includes the steps of increasing the variable gain if a second selected number (M) of peak values of the N cardiac events are below a selected low threshold and decreasing the variable gain if M peak values of the N cardiac events are above a selected high threshold.

50. A system for automatically controlling a gain of a cardioverter/defibrillator, which receives electrical activity of the heart and provides shock pulses in response thereto, the system comprising:

amplifier for amplifying the electrical activity of the heart according to a variable gain;

a cardiac depolarization detector for detecting depolarizations in the amplified electrical activity of the heart and providing a detect signal representing a cardiac event indicative of a depolarization when the amplified electrical activity exceeds a sensitivity threshold; and storing means for storing history information representative of the amplified electrical activity of a selected number of cardiac events;

gain controller for adjusting the variable gain in discrete steps based on the stored history information, and including means responsive to the detect signal to set the gain to a selected relatively high sensitivity based on a certain condition occurring which substantially invalidates the history information.

51. The system of claim 50 wherein the certain condition occurs when a cardiac event is not detected within a selected time period.

52. The system of claim 50 wherein the certain condition is a shock pulse being delivered by the cardioverter/defibrillator.

53. The system of claim 50 wherein the system automatically controls a gain of a cardioverter/defibrillator having pacing capability, and wherein the certain condition is a pacing pulse being delivered by the cardioverter/defibrillator.

54. The system of claim 50 wherein the gain controller adjusts the variable gain in discrete gain steps and the selected relatively high sensitivity is at least one discrete step from a maximum sensitivity.

55. The system of claim 54 further comprising means for decrementing the gain from the selected relatively high sensitivity by a selected number of discrete gain steps if the setting of the gain to the selected relatively high sensitivity creates a clipped peak value of the amplified electrical activity on the following detected cardiac event.

56. The system of claim 55 further comprising means for decrementing the gain by at least one discrete gain step if the peak value of the amplified electrical activity is still clipped on the second detected cardiac event following the setting of the gain to the selected relatively high sensitivity.

57. The system of claim 54 further comprising means for decrementing the gain from the selected relatively high sensitivity by a selected number of discrete gain steps if the setting of the gain to the selected relatively high sensitivity does not create a clipped peak value of the amplified electrical activity on the following detected cardiac event and does create a clipped peak value of the amplified electrical activity on the second detected cardiac event following the setting of the gain to the selected relatively high sensitivity.

58. The system of claim 51 wherein the selected time period is approximately 1.5 seconds.

59. The system of claim 50 wherein the gain controller comprises:

storage means for storing peak history information representative of peak values of the amplified electrical activity of a first selected number (N) of cardiac events; and adjusting means for adjusting the variable gain based on the stored peak history information.

60. The system of claim 59 wherein the adjusting means increases the variable gain if a second selected number (M) of peak values of the N cardiac events are below a selected low threshold and decreases the variable gain if M peak values of the N cardiac events are above a selected high threshold.

* * * * *